(12) United States Patent
Lee

(10) Patent No.: US 9,629,574 B2
(45) Date of Patent: Apr. 25, 2017

(54) MULTI-POSITION, MULTI-PARAMETER USER-WEARABLE SENSOR SYSTEMS AND METHODS FOR USE THEREWITH

(71) Applicant: Salutron, Inc., Fremont, CA (US)

(72) Inventor: Yong Jin Lee, Seoul (KR)

(73) Assignee: SALUTRON INC., Newark, CA (US)

( * ) Notice: Subject to any disclaimer, the term of this patent is extended or adjusted under 35 U.S.C. 154(b) by 0 days.

(21) Appl. No.: 14/792,386

(22) Filed: Jul. 6, 2015

(65) Prior Publication Data

US 2016/0317067 A1 Nov. 3, 2016

Related U.S. Application Data

(60) Provisional application No. 62/154,526, filed on Apr. 29, 2015.

(51) Int. Cl.
| | |
|---|---|
| *A61B 5/11* | (2006.01) |
| *A61B 5/00* | (2006.01) |
| *A61B 5/024* | (2006.01) |
| *A61B 5/0432* | (2006.01) |
| *A61B 5/053* | (2006.01) |

(52) U.S. Cl.
CPC .......... *A61B 5/1118* (2013.01); *A61B 5/0024* (2013.01); *A61B 5/1123* (2013.01); *A61B 5/02427* (2013.01); *A61B 5/0432* (2013.01); *A61B 5/0533* (2013.01); *A61B 5/0537* (2013.01); *A61B 5/486* (2013.01); *A61B 5/681* (2013.01); *A61B 2560/0209* (2013.01)

(58) Field of Classification Search
CPC ....... A61B 5/68; A61B 5/6801; A61B 5/6813; A61B 5/684; A61B 5/0002; A61B 5/11; A61B 5/1118; A61B 5/1123; A61B 2560/0209

See application file for complete search history.

(56) References Cited

U.S. PATENT DOCUMENTS

| | | |
|---|---|---|
| 4,371,945 A | 2/1983 | Karr et al. |
| 7,072,789 B2 | 7/2006 | Vock et al. |

(Continued)

FOREIGN PATENT DOCUMENTS

KR 10-2014-0191133 * 12/2014 ............ A61B 5/486

*Primary Examiner* — Andrew Bee
(74) *Attorney, Agent, or Firm* — Vierra Magen Marcus LLP

(57) ABSTRACT

A base station identifies user-wearable devices being worn by a user, wherein each of the user-wearable devices is battery powered, includes a plurality of sensors, performs wirelessly communication, and is worn on a separate portion of the user's body. For each of the user-wearable devices, the base station identifies a portion of the user's body on which the user-wearable device is being worn. The base station also identifies an activity in which the user is engaged, and identifies multiple types of sensor data to be sensed using the sensors of the user-wearable devices, to enable tracking of metric(s) relevant to the activity in which the user is engaged. The base station determines how to distribute sensing responsibilities for the multiple types of sensor data among the sensors of the user-wearable devices being worn by the user, and selectively activates and deactivates individual sensors of each of the user-wearable devices.

25 Claims, 8 Drawing Sheets

(56) References Cited

U.S. PATENT DOCUMENTS

| | | | |
|---|---|---|---|
| 8,684,900 B2* | 4/2014 | Tran | A61B 8/488 600/3 |
| 2008/0284650 A1 | 11/2008 | MacIntosh et al. | |
| 2011/0054782 A1 | 3/2011 | Kaahui | |
| 2011/0131012 A1 | 6/2011 | Czaja et al. | |
| 2012/0188158 A1* | 7/2012 | Tan | A61B 5/0488 345/156 |
| 2012/0191405 A1 | 7/2012 | Molyneux et al. | |
| 2012/0277040 A1 | 11/2012 | Vincent et al. | |
| 2013/0332286 A1 | 12/2013 | Medelius et al. | |
| 2014/0031703 A1 | 1/2014 | Rayner et al. | |
| 2014/0277633 A1 | 9/2014 | Flaction | |
| 2016/0157718 A1* | 6/2016 | Barnes | A61B 5/0024 600/479 |
| 2016/0183869 A1* | 6/2016 | Oh | A61B 5/7475 600/595 |
| 2016/0189450 A1* | 6/2016 | Anderson | G07C 9/00103 340/5.51 |

\* cited by examiner

MULTI-POSITION, MULTI-PARAMETER USER-WEARABLE SENSOR SYSTEMS AND METHODS FOR USE THEREWITH

PRIORITY CLAIM

This application claims priority to U.S. Provisional Patent Application No. 62/154,526, filed Apr. 29, 2015, which is incorporated herein by reference.

BACKGROUND

Athletes and other persons wishing to monitor their health and/or athletic performance often desire to obtain or monitor data pertaining to their physical activities, accomplishments and/or condition. In some situations, a physician, a coach or a software application may prescribe certain steps or exercises to be performed by a person under certain conditions, such as performing an exercise at or near a certain heart rate. The physician, coach or software application and/or the athlete or other person may wish to gather data regarding the performance of the exercises, the conditions under which the exercises were performed, and/or how the athlete or other person is responding to the exercises. For example, an athlete who can correlate different training or exercise techniques with improved performance metrics can become faster, stronger, or exert more force in an action, such as hitting a ball harder. Athletes, patients and anyone else associated with a physical activity can benefit from improved techniques for gathering, monitoring, correlating, analyzing, using, interpreting, and making decisions based on physical activity data, or more generally, sensor data obtained from user wearable devices.

Sensor data, including physiological data and motion data, can be obtained from battery powered user-wearable devices including sensors adapted to obtain such data. For example, a person can wear multiple user-wearable devices including sensors on various portions of their body so that such devices can obtain various different types of sensor data. However, if such devices all operate independently of one another, in a non-coordinated manner, such devices may waste limited resources and/or not obtain the data useful for monitoring metrics relevant to activities in which persons are engaged.

DETAILED DESCRIPTION

Figure 1A:
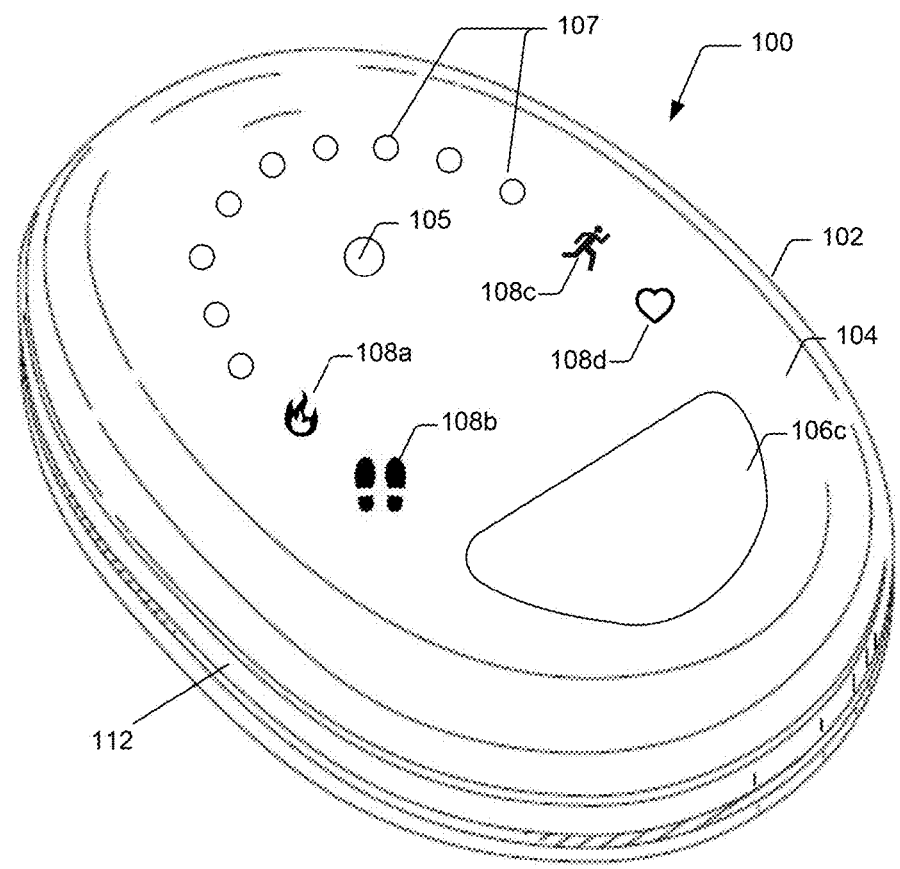
FIGS. 1A, 1B and 1C are, respectively, perspective, side and rear views of a physiological sensor pod according to an embodiment of the present technology.

In the following detailed description, reference is made to the accompanying drawings that form a part hereof, and in which is shown by way of illustration specific illustrative embodiments. It is to be understood that other embodiments may be utilized and that mechanical and electrical changes may be made. The following detailed description is, therefore, not to be taken in a limiting sense. In the description that follows, like numerals or reference designators will be used to refer to like parts or elements throughout. In addition, the first digit of a reference number identifies the drawing in which the reference number first appears.

Figure 1B:
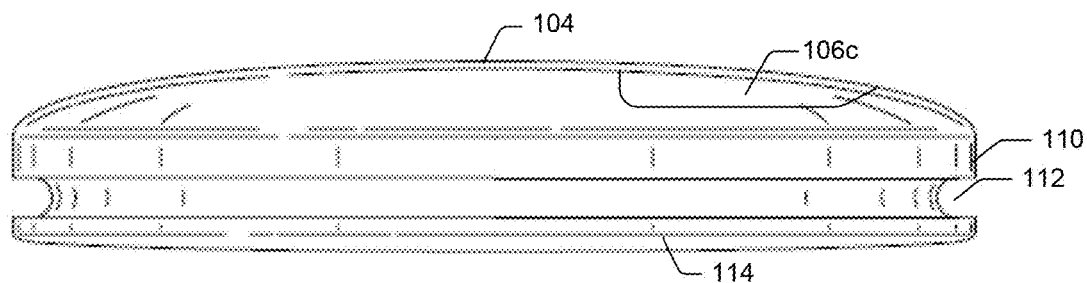
Figure 1C:
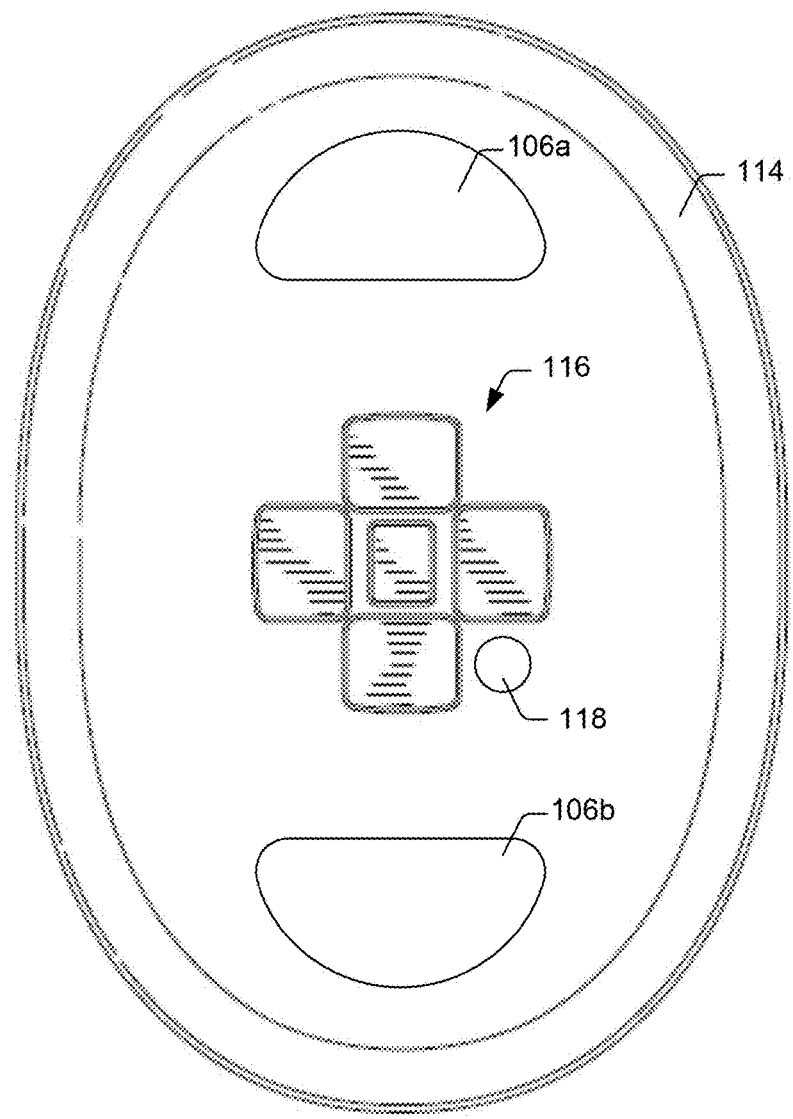

FIGS. 1A, 1B and 1C are, respectively, perspective, side and rear views of a physiological sensor pod 100 according to an embodiment of the present technology. The physiologic sensor pod 100 is an example of a user-wearable device, and thus, can be referred to more succinctly as a sensor pod 100, or can be referred to more generally as a sensor device 100, a user-wearable device 100, or simply a device 100. The sensor pod 100 is shown as including a housing 102 having a top surface 104, a bottom surface 114 and a peripheral surface 110 extending between the top surface 104 and the button surface 114. The housing 102 also includes a groove 112 within and extending about the peripheral surface 110. A battery, and electronic circuitry, including, but not limited to, a processor, memory, a wireless interface, switch circuitry, and a battery charging unit are located within the housing 102, as will be described in additional detail below. The housing 102 can be made of a plastic, a carbon composite, aluminum or some other metal, or combinations thereof, but is not limited thereto.

Where one or more light emitting elements and/or one or more light detectors are located within the housing 102, and the material of which a majority of the housing 102 is made is not light transmissive, the housing can include light transmissive windows (e.g., made of a clear or other light transmissive material) that allows light to enter and/or exit through the housing windows. The housing 102 can be made in two parts (e.g., a top part and a bottom part) that are connected together to encase the battery and electronic circuitry of the sensor pod 100. Where the housing 102 is made in two parts, the two parts can be primarily made of the same material, or of different materials.

In accordance with specific embodiments, the sensor pod 100 can wirelessly communicate with a base station (e.g., 352 in FIG. 3), which can be a mobile computing device (e.g., smart phone, a tablet computer, a personal data assistant (PDA) or a laptop computer), a desktop computer, or some other computing device that is capable of performing wireless communication. More specifically, the sensor pod can include a wireless interface that enables it to communicate with and sync with a base station. The base station can, e.g., include a health and fitness software application and/or other applications, which can be referred to as apps. The sensor pod 100 can upload, and more specifically, transmit, data obtained by the sensor pod 100 to the base station, so that such data can be used by a health and fitness software application and/or other apps stored on and executed by the base station.

Referring specifically to FIG. 1A, the top surface 104 of the housing 102 includes an optional top electrode 106c. In the embodiment shown, the top surface 104 of the housing 102 includes a goal indicator 107, which is shown as comprising a plurality of individually activateable light emitting elements arranged in a semicircle. The light emitting elements of the goal indicator 107 are preferably located within the housing 102, but are viewable through the top surface 104 of the housing 102. The top surface 104 of the housing 102 further includes a plurality of mode indicator icons 108a, 108b, 108c and 108d, which are used to indicate the present operational mode of the sensor pod 100. The mode indicator icons are shown as including a calories burned icon 108a, a walking icon 108b, a running icon 108c and a heart icon 108d. Light emitting elements within the housing 102, below the mode indicator icons 108a, 108b, 108c and 108d, can selectively emit light to illuminate one of the icons to indicate the mode in which the sensor pod 100 is operating. A user, through use of a base station (e.g., 352 in FIG. 3), can select the mode, or the sensor pod 100 or base station may select the mode based on data obtained from various sensors, algorithms, apps and/or the like. Although not shown, the housing 102 of the sensor pod 100 can optionally include a digital display that can be used, e.g., to display the time, date, day of the week and/or the like, and can also be used to display activity and/or physiological metrics, such as, but not limited to, heart rate (HR), heart rate variability (HRV), calories burned, steps taken, distance walked and/or run, and/or sleep metrics. In other embodiments, the sensor pod itself does not include any indicators or display, but rather, all information that is provided to a user is provided via the base station that is in wireless communication with the sensor pod(s).

The housing 102, and more generally the sensor pod 100, can optionally also include an outward facing ambient light sensor (ALS) 105, which can be used to detect ambient light, and thus, can be useful for detecting whether it is daytime or nighttime, as well as for other purposes. Where the sensor pod 100 includes an ALS 105, the ALS can be placed behind a light transmissive window in the upper surface of the housing 102. Such an ALS 105 can include one or more photodetector, each of which can be a photoresistor, photodiode, phototransistor, photodarlington or avalanche photodiode, but is not limited thereto.

Referring now to FIG. 1C, the bottom surface 114 of the housing 102 is shown as including a pair of spaced apart electrodes 106a and 106b, and plurality of light transmissive windows 116 for one or more light emitting elements and one or more light detecting elements of a photoplethysmography (PPG) sensor, discussed in more detail below. Additionally, the bottom surface of the housing 102 is shown as including a thermally conductive metal contact 118 for a skin temperature sensor, also discussed in more detail below. The thermally conductive metal contact 118 can be made of aluminum or copper, but is not limited thereto. Exemplary electrical components and modules that can be included within the housing 102 of the sensor pod 100 are shown in and described below with reference to FIG. 3.

In accordance with an embodiment, the housing 102 is water tight and water proof, or at least water resistant. More generally, the sensor pod 100 is water tight or water resistant so that it can get wet and still operate. In accordance with an embodiment, to increase a probability that the sensor pod 100 remains water tight, the sensor pod 100 is designed such that once it is manufactured its housing 102 is not intended to be opened. For example, the housing 102 can be hermetically sealed. Accordingly, in such an embodiment the battery (e.g., 310 in FIGS. 3 and 4) is not replaceable, but rather, is only rechargeable. In other embodiments, the battery is replaceable.

Figure 2A:
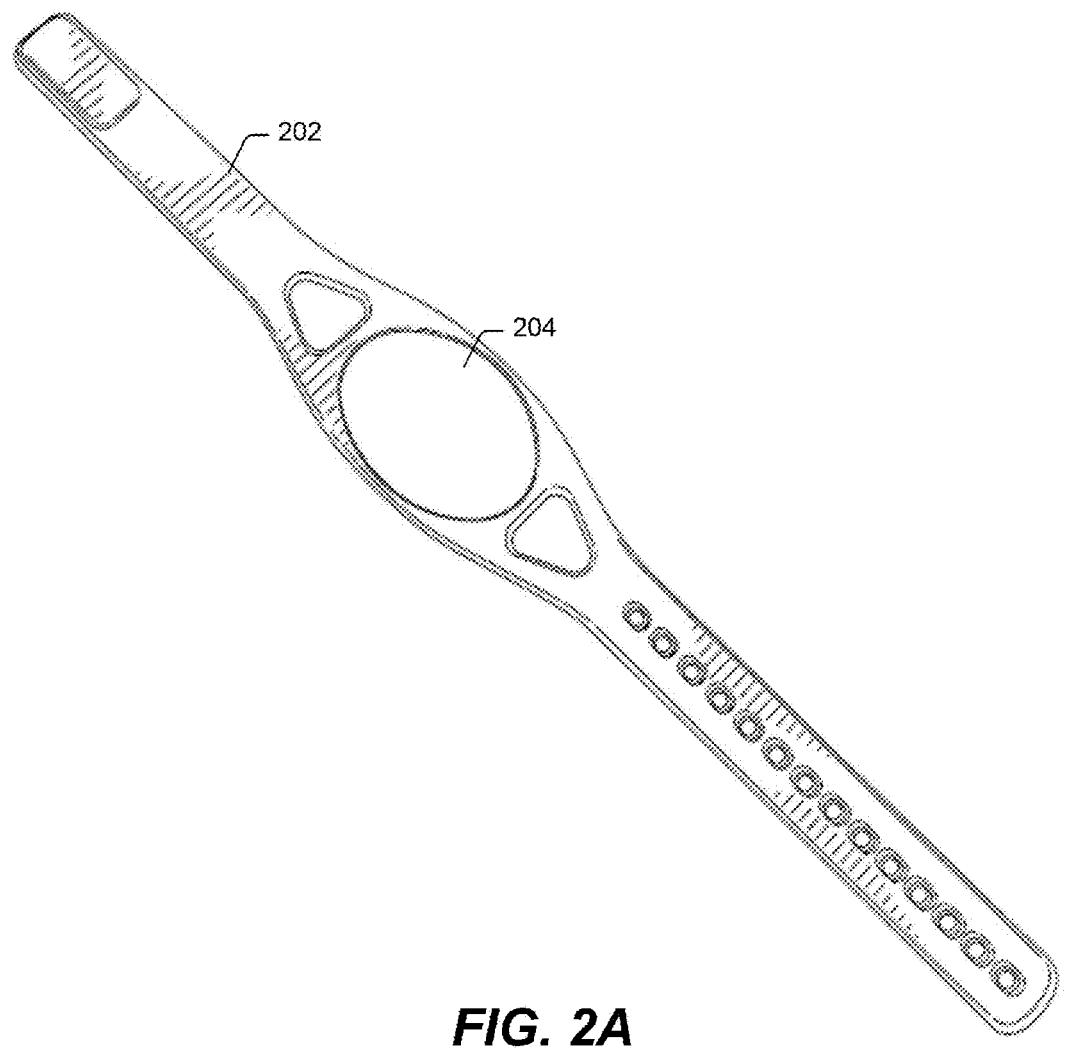
FIG. 2A illustrates a wrist band including an opening into which the physiological sensor pod introduced in FIGS. 1A, 1B and 1C can be inserted.
Figure 2B:
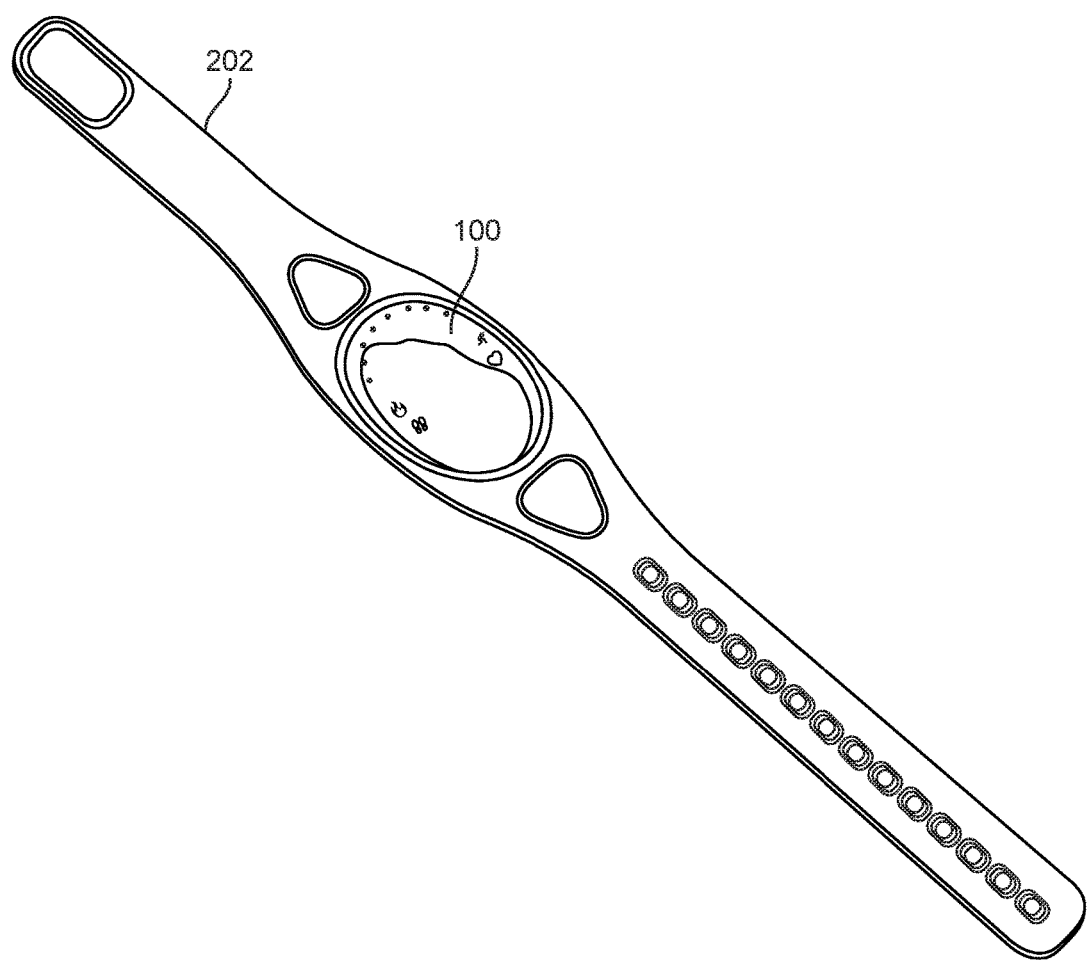
FIG. 2B illustrates the wrist band of FIG. 2A with the sensor pod introduced in FIGS. 1A, 1B and 1C inserted within the opening of the wrist band.

FIG. 2A illustrates a wrist band 202 that includes an opening 204 into which the groove 112 of the sensor pod 100 fits to secure sensor pod 100 in place. FIG. 2B illustrates the wrist band 202 with the sensor pod 100 secured within the opening 204. The sensor pod 100 can alternatively be placed in a similar opening in a chest strap, headband, swim cap, arm band, or some other user wearable band, strap, article of apparel or device. For example, a chest strap that is intended to strap the sensor pod 100 to a person's chest may resemble the wrist band 202 shown in FIGS. 2A and 2B, but would be longer in length to enable the strap to fit around a person's chest. In still other embodiments, the sensor pod 100 can be placed into a pocket within a sock or tight fitting shirt (e.g., a bicycle shirt) or other article of apparel or clothing that includes a pocket for the sensor pod. Such a pocket can include an opening that enables the backside of the sensor pod, which includes windows for a PPG or other optical sensor, electrodes or other sensor elements, to contact the wearer's skin to thereby enable the sensor(s) to operate properly. The opening in the pocket can also enable the groove 112 in the sensor pod 100 to be snapped into a correct position and held in place against a user's skin. The sensor pod 100 can alternatively be placed in an opening, slot and/or pocket in headband, a helmet (e.g., a bicycle, motorcycle, skateboard, football, baseball, hockey, snowboard or ski helmet) or other headwear (e.g., a beanie, a baseball cap or any other type of hat). The sensor pod 100 may alternatively be placed in an opening, slot and/or pocket in a pair of glasses or a head mounted display (HMD) that positions the back surface 114 of the sensor pod 100 against a user's temple or forehead.

Figure 3:
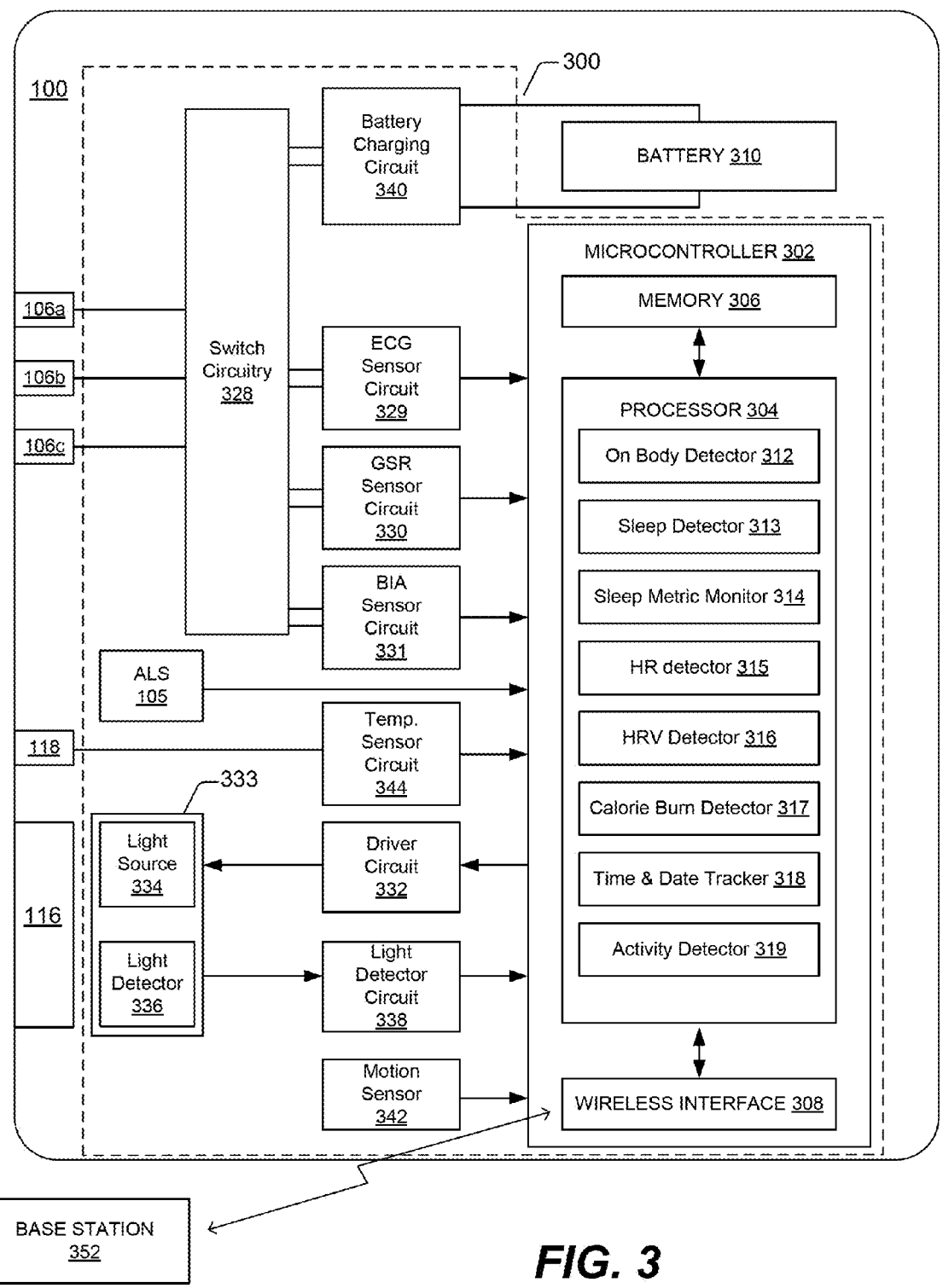
FIG. 3 depicts an example block diagram of electrical components that are located within the housing of the physiological sensor pod introduced in FIGS. 1A, 1B and 1C, according to an embodiment of the present technology.

FIG. 3 depicts a block diagram of electrical components 300 of the sensor pod 100, according to an embodiment, which are located within the housing 102 of the sensor pod 100. More specifically, the components within the dashed block labeled 300 are exemplary electrical components of the sensor pod 100, which are powered by the battery 310. Referring to FIG. 3, the sensor pod 100 is shown as including a microcontroller 302 that includes a processor 304, memory 306 and a wireless interface 308. It is also possible that the memory 306 and wireless interface 308, or portions thereof, are external the microcontroller 302. Other electronic components 300 of the sensor pod 100 can include, but are not limited to, a battery charging circuit 340, an electrocardiogram (ECG) sensor circuit 329, a galvanic skin resistance (GSR) sensor circuit 330, a bioimpedance analysis (BIA) sensor circuit 331, a driver circuit 332, a light detector circuit 338, a motion sensor 342, a photoplethysmography (PPG) sensor 333, a temperature sensor circuit 344, and the optional ALS 105. It is also possible that electronic components 300 include more or less components than shown. The battery 310 is used to power the various components of the sensor pod, and a battery charger circuit 340 is used to charge the battery 310. While not specifically shown, the sensor pod 100 can also include one or more voltage regulators that are used to step-up and or step-down the voltage provided by the battery 310 to appropriate levels to power the various components of the sensor pod 100. The microcontroller 302, or the processor 304 thereof, receives signals from the various sensors and sensor circuits, or more generally, from the various circuitry.

At the left in FIG. 3 are small rectangular blocks that schematically represent the electrodes 106a, 106b and 106c and the temperature sensor contact 118, introduced above in the discussion on FIGS. 1A and 1C. The temperature sensor contact 118 is shown as being connected to the temperature sensor circuit 344. The electrodes 106a, 106b and 106c can be referred to collectively as electrodes 106, or individually as an electrode 106. For simplicity, in FIG. 3 the optional electrode 106c is shown as being next to the electrodes 106a and 106b. However, as can be appreciated from FIGS. 1A and 1C, the electrode 106c is remotely located relative to the electrodes 106a and 106b. More specifically, the electrodes 106a and 106b are located on the bottom surface 114 of the housing 102, as shown in FIG. 1C, and the optional electrode 106c is optionally located on the top surface 104 of the housing 102, as shown in FIG. 1A. Alternatively, the optional electrode 106c can be located on an upper portion of the peripheral surface 110 of the housing 102, so long as it does interfere with the groove 112 and is accessible (e.g., can be touched by a user's finger) when the sensor pod 100 is inserted within an opening in a wrist band (e.g., 202 in FIGS. 2A and 2B), chest band or other apparel that enables a user to wear the sensor pod 100. More generally, FIG. 3 is not intended to show the precise locations of the various sensors, electrodes, contact, electrical components, windows, etc. of the sensor pod 100.

Also shown at the left in FIG. 3 is a block representing the window(s) 116 for a light source 334 and a light detector 336 of a photoplethysmography (PPG) sensor 333. The PPG sensor 333 includes the light source 334 that is driven by a driver circuit 332, and the light detector 336 whose output is provided to a light detector circuit 338. The driver circuit 332 can be controlled by the microcontroller 302 or the processor 304 thereof. The driver circuit 332 can include, e.g., a current source and a switch that selectively provides the current produced by the current source to the light source 334. An output of the light detector circuit 338 can be provided to the microcontroller 302 or the processor 304 thereof. The light source 334 can include one or more light emitting elements, each of which can be a light emitting diode (LED), incandescent lamp or laser diode, but is not limited thereto. While it is preferred that the light source 334 emit infrared (IR) light, because the human eye cannot detect IR light, the light source 334 can alternatively produce light of other wavelengths. The light detector 336 can include one or more photodetectors (also referred to as light detecting elements), each of which can be a photoresistor, photodiode, phototransistor, photodarlington or avalanche photodiode, but is not limited thereto. In accordance with an embodiment, the light source 334 includes a single IR LED, and the light detector 336 includes four photodiodes arranged around the single IR LED. For example, referring briefly back to FIG. 1C, the center one of the windows 116 can allow light to be emitted by the single IR LED, and the four other windows 116 surrounding the center window can allow reflected/scattered light to be incident of the four photodiodes that surround the single IR LED.

Referring again to FIG. 3, the light source 334 is selectively driven by the driver circuit 332 to emit light. When the light source 334 emits light a portion of the emitted light is reflected or backscattered by patient tissue, and reflected/backscattered light is received by the light detector 336. In this manner, changes in reflected light intensity are detected by the light detector 336, which outputs a PPG signal indicative of the changes in detected light, which are indicative of changes in blood volume. The light detector circuit 338 can, e.g., convert the PPG signal output by the light detector 336 from a current signal to a voltage signal, and filter and/or amplify the PPG signal. Additionally, the PPG signal can be converted to a digital signal using an analog-to-digital converter (ADC), if the PPG signal is to be analyzed in the digital domain. Such an ADC can be part of the light detector circuit 338, part of the microcontroller 302, are independent thereof. Each cardiac cycle in the PPG signal generally appears as a peak, thereby enabling the PPG signal to be used to detect peak-to-peak intervals, which can be used to calculate heart rate (HR) and heart rate variability (HRV). In accordance with certain embodiments, the light source 334 emits light of two different wavelengths that enables non-invasive monitoring of arterial oxygen saturation using pulse oximetry techniques.

The sensor pod 100 is also shown as including a motion sensor 342. In accordance with an embodiment the motion sensor 342 is an accelerometer. The accelerometer can be a three-axis accelerometer, which is also known as a three-dimensional (3D) accelerometer, but is not limited thereto. The accelerometer may provide an analog output signal representing acceleration in one or more directions. For example, the accelerometer can provide a measure of acceleration with respect to x, y and z axes. The motion sensor 342 can alternatively be a gyrometer, which provides a measure of angular velocity with respect to x, y and z axes. It is also possible that the motion sensor 342 is an inclinometer, which provides a measure of pitch, roll and yaw that correspond to rotation angles around x, y and z axes. It is also possible the sensor pod 100 includes multiple different types of motion sensors, some examples of which were just described. Depending upon the type(s) of motion sensor(s) used, such a sensor can be used to detect the posture of a portion of a user's body (e.g., a wrist, ankle, chest or head) on which the sensor pod 100 is being worn. The output(s) of the motion sensor 342 can be provided to the microcontroller 302 or the processor 304 thereof.

The wireless interface 308 can wireless communicate with a base station (e.g., 352), which as mentioned above, can be, e.g., a smart phone, a tablet computer, a PDA, a laptop computer, a desktop computer, or some other computing device that is capable of performing wireless communication. The wireless interface 308, and more generally the sensor pod 100, can communicate with a base station 352 using various different protocols and technologies, such as, but not limited to, Bluetooth™, Wi-Fi™, ZigBee™ or ultrawideband (UWB) communication. In accordance with an embodiment, the wireless interface 308 comprises telemetry circuitry that include a radio frequency (RF) transceiver electrically connected to an antenna (not shown), e.g., by a coaxial cable or other transmission line. Such an RF transceiver can include, e.g., any well-known circuitry for transmitting and receiving RF signals via an antenna to and from an RF transceiver of a base station 352.

The switch circuitry 328 enables these various sensor circuits, including the ECG sensor circuit 329, the GSR sensor circuit 330 and the BIA sensor circuit 331 to share the same electrodes 106. In an embodiment, the microcontroller 302 (or some other controller) produces one or more switch control signals that selectively control how and when individual ones (or subsets of) the electrodes 106 is/are connected to the various inputs of the sensor circuits 329, 330 and 331. In an embodiment, the switch circuitry 328 can also be used to selectively connect the two bottom electrodes 106a and 106b to the battery charging circuit 340. More generally, the switch circuitry 328 enables two (or more) of the same electrodes 106 to be used, albeit at different times, by the battery charging circuit 340 and one or more sensor circuits (e.g., 329, 330 and 331). Alternatively, each of the sensor circuits 329, 330 and 331 can have their own dedicated electrodes.

The ECG sensor circuit 329 can be used to sense an ECG signal between the two bottom electrodes 106a and 106b when the electrodes 106a and 106b are contact with a person's chest. When the two bottom electrodes 106a and 106b of the sensor pod 100 are against another portion of a person's body (e.g., a person's wrist), instead of against a person's chest, an ECG signal cannot be sensed between the two bottom electrodes 106a and 106b. The ECG sensor circuit 329 (or another ECG sensor circuit) can alternatively be used to sense an ECG signal between at least one of the bottom electrodes 106a, 106b that is in contact with a person's skin (e.g., on their wrist) and the top (or side) electrode 106c that is in contact with another portion of the person's skin (e.g., a finger on the opposite hand). In other words, an ECG signal can be sensed when one (or both) of the electrodes 106a, 106b are in contact with a user's arm (or other body part) and the electrode 106c is in contact with a user's finger on their other arm, in which case a circuit is completed that extends across the user's chest cavity that includes their heart. The ECG sensor circuit 329 can include one or more low power, precision amplifiers with programmable gain and/or automatic gain control, bandpass filtering, and a threshold detection circuit, as known in the art, to selectively sense an ECG signal of interest.

The GSR sensor circuit 330 can be used to sense a galvanic skin resistance between a pair of the electrode 106 (e.g., the electrodes 106a and 106b) that are in contact with a person's skin. The galvanic skin resistance measurement will be relatively low when a user is wearing the sensor pod 100 such that the electrodes 106a and 106b are against their skin. By contrast, the galvanic skin resistance measurement will be very high when the electrodes 106a and 106b are not in contact with the user's skin. The galvanic skin resistance measurement, which can also be referred to as a galvanic skin response, may also vary based on levels perspiration.

The BIA sensor circuit 408 is used to measure impedance, at one or more frequencies, between a pair of the electrodes 106 (e.g., the electrodes 106a and 106b) that are in contact with a person's skin.

Still referring to FIG. 3, the sensor pod 100 is shown as including various detectors or trackers, including an on-body detector 312, a sleep detector 313, a sleep metric detector 314, a heart rate (HR) detector 315, a heart rate variability (HRV) detector 316, a calorie burn detector 317, a time and date tracker 318 and an activity detector 319. The various detectors and trackers may communicate with one another, as will be explained below. Each of these detectors and trackers 312, 313, 314, 315, 316, 317, 318 and 319 can be implemented using software, firmware and/or hardware. It is also possible that some of these detectors and trackers are implemented using software and/or firmware, with others implemented using hardware. Other variations are also possible. In accordance with a specific embodiments, each of these detectors or trackers 312, 313, 314, 315, 316, 317, 318, 319 is implemented using software code that is stored in the memory 306 and is executed by the processor 304. The memory 306 is an example of a tangible computer-readable storage apparatus or memory having computer-readable software embodied thereon for programming a processor (e.g., 304) to perform a method. For example, non-volatile memory can be used. Volatile memory such as a working memory of the processor 304 can also be used. The computer-readable storage apparatus may be non-transitory and exclude a propagating signal.

The on-body detector 312 uses signals and/or data obtained from one or more of the above described sensors and/or sensor circuits to determine whether the sensor pod 100 is being worn by a user (also referred to herein as a person). For example, the on-body detector 312 can use signals/and/or data obtained from the light source 334 and light detector 336 (which can collectively be referred to as a PPG sensor 333), the GSR sensor circuit 406, the temperature sensor circuit 344 and/or the motion sensor 342 to determine whether the sensor pod 100 is being worn by a user. The on-body detector 312 can be used to selective operate the sensor pod 100 in a low power mode when the on-body detector 312 detects that the sensor pod 100 is not being worn by a user. Additional details of the on-body detector 212 are described in U.S. patent application Ser. No. 14/341,248, titled "User-Wearable Devices with Power Conserving Features," which was filed Jul. 24, 2014.

The sleep detector 313 uses signals and/or data obtained from one or more of the above described sensors to determine whether a user, who is wearing the sensor pod 100, is sleeping. For example, signals and/or data obtained using the motion sensor 342 can be used to determine when a user is sleeping. This is because people typically move around less when sleeping compared to when awake. For another example, if the sensor pod 100 includes an outward facing ambient light sensor (ALS) (e.g., 105 in FIG. 1A) then signals and/or data obtained using the outward facing ALS can additionally or alternatively be used to determine when a user is sleeping. This is because people typically sleep in a relatively dark environment with low levels of ambient light. Additionally, if the user's arm posture can be detected from the motion sensor 342, then information about arm posture can also be used to detect whether or not a user is sleeping. The sleep detector 313 can also be used to detect when a user, who is wearing the sensor pod 100, wakes up, as well as when the user is awake.

The sleep metric detector 314 uses signals and/or data obtained from one or more of the above described sensors and/or other detectors and trackers to quantify metrics of sleep, such as total sleep time, sleep efficiency, number of awakenings, and estimates of the length or percentage of time within different sleep states, including, for example, rapid eye movement (REM) and non-REM states. The sleep metric detector 314 can, for example, use signals and/or data obtained from the motion sensor 342 and/or from the HR detector 315 to distinguish between the onset of sleep, non-REM sleep, REM sleep and the user waking from sleep. One or more quality metric of the user's sleep can then be determined based on an amount of time a user spent in the different phases of sleep. Such quality metrics can be uploaded to a base station (e.g., 352) for display and/or further analysis. Additionally, or alternatively, if the sensor pod 100 included a digital display, such metrics can be displayed on such a digital display.

The HR detector 315 can use signals and/or data obtained from the PPG sensor 333 to detect HR. For example, the PPG sensor 333 can be used to obtain a PPG signal from which peak-to-peak intervals can be detected, which can also be referred to as beat-to-beat intervals. Additionally, or alternatively, beat-to-beat intervals can be determined from an ECG signal obtained using an ECG sensor circuit (e.g., 402 or 404 in FIG. 4) by measuring the time interval between R-waves or other features of the ECG signal. The beat-to-beat intervals, which are intervals between heart beats, can be converted to HR using the equation HR=(1/beat-to-beat interval)*60. Thus, if the beat-to-beat interval=1 sec, then HR=60 beats per minute (bpm); or if the beat-to-beat interval=0.6 sec, then HR=100 bpm. In an embodiment, the HR detector 315 can measure the beat-to-beat intervals of a PPG signal, and also measure the beat-to-beat intervals of an ECG signal, and use an average of the two types of beat-to-beat intervals to detect HR. In another embodiment, there can be a determination of whether a PPG signal or an ECG signal has a greater to signal-to-noise ratio (SNR), and which ever one of the PPG and ECG signals has a greater SNR can be used by the HR detector 315 to detect HR. The user's HR can be uploaded to a base station (e.g., 352) for display and/or further analysis. Additionally, or alternatively, if the sensor pod 100 included a digital display, HR or information indicative can be displayed on such a digital display. In certain embodiments, rather than the sensor pod 100 itself determining a user's HR, data indicate of an ECG signal (also referred to as ECG signal data or ECG data) and/or data indicative of a PPG signal (also referred to as PPG signal data or PPG data) that is obtained by the sensor pod 100 is transmitted to a base station (e.g., 352 in FIG. 3), and the base station determines the user's HR based on the ECG and/or PPG signal data it obtains from the sensor pod.

The HRV detector 316 can use signals and/or data obtained from the PPG sensor 333 and/or one of the ECG sensor circuits 402 or 404 to detect HRV. For example, in the same manner as was explained above, beat-to-beat intervals can be determined from a PPG signal obtained using the PPG sensor 333. Additionally, or alternatively, beat-to-beat intervals can be determined from an ECG signal obtained using an ECG sensor circuit (e.g., 402 or 404 in FIG. 4) by measuring the time interval between R-waves or other features of the ECG signal. HRV can be determined by calculating a measure of variance, such as, but not limited to, the standard deviation (SD), the root mean square of successive differences (RMSSD), or the standard deviation of successive differences (SDSD) of a plurality of consecutive beat-to-beat intervals. Alternatively, or additionally, an obtained PPG signal and/or ECG signal can be converted from the time domain to the frequency domain, and HRV can be determined using well known frequency domain techniques. In an embodiment, the HRV detector 316 can measure the beat-to-beat intervals of a PPG signal, and also measure the beat-to-beat intervals of an ECG signal, and use an average of the two types of beat-to-beat intervals to detect HRV. In another embodiment, there can be a determination of whether a PPG signal or an ECG signal has a greater to signal-to-noise ratio (SNR), and which ever one of the PPG and ECG signals has a greater SNR can be used by the HRV detector 316 to detect HRV. The user's HRV can be uploaded to a base station (e.g., 352) for display and/or further analysis. Additionally, or alternatively, if the sensor pod 100 included a digital display, HRV or information indicative thereof can be displayed on such a digital display. In certain embodiments, rather than the sensor pod 100 itself determining a user's HRV, data indicate of an ECG signal (also referred to as ECG signal data or ECG data) and/or data indicative of a PPG signal (also referred to as PPG signal data or PPG data) that is obtained by the sensor pod 100 is transmitted to a base station (e.g., 352 in FIG. 3), and the base station determines the user's HRV based on the ECG and/or PPG signal data it obtains from the sensor pod.

The calorie burn detector 317 can determine a current calorie burn rate and an amount of calories burned over a specified amount of time based on motion data obtained using the motion sensor 342, HR as determined using the HR detector 315, and/or skin temperature as determined using the skin temperature sensor 340. A calorie burn rate and/or an amount of calories burned can uploaded to a base station (e.g., 252) for display and/or further analysis. Additionally, or alternatively, if the sensor pod 100 included a digital display, such information can be displayed on such a digital display. The goal indicator 107, shown in FIG. 1A, can also be used to inform a user of how close they are to reaching a calories burned goal.

The time and date tracker 318 can keep track of the time of day, date, and/or the like. The time and date tracker 318 of the sensor pod 100 can be synced with a similar tracker of the base station 352. The time and data tracker 318 can provide time of day and date information to the other detectors described herein and/or can be used to date and/or time stamp collected data.

The activity detector 319 can determine a type and amount of activity of a user based on information such as, but not limited to, motion data obtained using the motion sensor 342, heart rate as determined by the HR detector 315, skin temperature as determined by the skin temperature sensor 340, and time of day. The activity detector 319 can use motion data, obtained using the motion sensor 342, to determine the number of steps that a user has taken with a specified amount of time (e.g., 24 hours), as well as to determine the distance that a user has walked and/or run within a specified amount of time. Activity metrics, or raw sensor data useful for determining such activity metrics, can be uploaded to a base station (e.g., 252) for display and/or further analysis. Additionally, or alternatively, if the sensor pod 100 included a digital display, such metrics can be displayed on such a digital display. The goal indicator 107, shown in FIG. 1A, can also be used to inform a user of how close they are to reaching an activity related goal, which can be a steps goal or a distance goal. In certain embodiments, rather than the sensor pod 100 itself determining a type and amount of activity of a user based on information such as, but not limited to, motion data obtained using the motion sensor 342, heart rate as determined by the HR detector 315, skin temperature as determined by the skin temperature sensor 340, and time of day, such information can be transmitted from the sensor pod 100 to a base station (e.g., 352 in FIG. 3), and the base station can determine the type and amount of activity of a user based on information it obtains from the sensor pod.

The sensor pod 100 can include less modules than shown in FIG. 3, more modules than show and/or alternative types of modules. For example, the sensor pod 100 can also include a body water content module and/or a body fat content module that calculates the user's body water content and/or body fat percentage based on measurements obtained using the BIA sensor circuit 408. Alternatively, the base station 352 can calculate body water content and/or body fat content based on data obtained using the BIA sensor circuit 408 of the sensor pod 100. For another example, the sensor pod 100 can include a stress module that estimates a user's stress level based on measures obtained using the GSR sensor circuit 406, one of the ECG sensor circuits 402, 404 and/or the skin temperature sensor circuit 344. Alternatively, the base station 352 can estimate the user's stress level based on data obtained from the GSR sensor circuit 406, one of the ECG sensor circuits 402, 404 and/or the skin temperature sensor circuit 344 of the sensor pod 100. Such modules can alternatively, or additionally, be included in a base station (e.g., 352 in FIG. 3).

The sensor pod 100 can also include respiration module that determines respiration rate from a PPG signal obtained using the PPG sensor 333 and/or from the ECG signal obtained using an ECG sensor circuit 402 or 404. For another example, a blood pressure module can determine blood pressure from PPG and ECG signals by determining a metric of pulse wave velocity (PWV) and converting the metric of PWV to a metric of blood pressure. More specifically, a metric of PWV can be determining by determining a time from a specific feature (e.g., an R-wave) of an obtained ECG signal to a specific feature (e.g., a maximum upward slope, a maximum peak or a dicrotic notch) of a simultaneously obtained PPG signal. An equation can then be used to convert the metric of PWV to a metric of blood pressure. These are just a few examples of other types of modules or detectors that can be included within sensor pod 100, which are not intended to be all encompassing.

Referring again to FIG. 3, the microcontroller 302, or the processor 304 thereof, can determine which switches of the switch circuitry 328 to open and close based on which mode the sensor pod 100 is operating in, or more generally, which parameters the sensor pod 100 is instructed to measure. For example, when the sensor pod 100 is in a HR or HRV detection mode, and the sensor pod 100 is resting against a person's chest (such that the electrodes 106a and 106b are contacting the person's skin), the switch circuitry 328 can connect the electrodes 106a and 106b, respectively, to first and second inputs of the ECG sensor circuit 329. For another example, when the sensor pod 100 is in a HR or HRV detection mode, and the sensor pod 100 is strapped to a person's wrist (e.g., using the wrist band 202 in FIGS. 2A and 2B), then the switch circuitry 328 can connect electrode 106a and/or 106b to a first input of the ECG sensor circuit 329 and the 106c electrode to a second input of the ECG sensor circuit 329. When the sensor pod 100 needs to measure galvanic skin resistance, and the sensor pod 100 is resting against a person's chest (such that the electrodes 106a and 106b are contacting the person's skin), the switch circuitry 328 can connect the electrodes 106a and 106b, respectively, to first and second inputs of the GSR sensor circuit 330. When the sensor pod 100 needs to measure galvanic skin resistance and the sensor pod 100 is strapped to a person's wrist (e.g., using the wrist band 202 in FIGS. 2A and 2B), the switch circuitry 328 can connect the electrode 106a and/or the electrode 106b to a first input of the GSR sensor circuit 330 and the electrode 106c to a second input of the GSR sensor circuit 330. When the sensor pod 100 needs to measure bioimpedance, and the sensor pod 100 is resting against a person's chest (such that the electrodes 106a and 106b are contacting the person's skin), the switch circuitry 328 can connect the electrodes 106a and 106b, respectively, to first and second inputs of the BIA sensor circuit 331. When the sensor pod 100 needs to measure bioimpedance and the sensor pod 100 is strapped to a person's wrist (e.g., using the wrist band 202 in FIGS. 2A and 2B), the switch circuitry 328 can connect the electrode 106a and/or the electrode 106b to a first input of the BIA sensor circuit 331 and the electrode 106c to a second input of the BIA sensor circuit 331. The sensor pod 100 itself can decide when to change modes. Alternatively, or additionally, a base station (e.g., 352) in wireless communication with the sensor pod 100 can select which mode the sensor pod 100 is operating in. As will be described in additional detail below, a base station (e.g., 352) can selectively activate and deactivate individual sensors within the sensor pod 100 by transmitting signal to the sensor pod 100 that instructs the sensor pod which sensors are to be activated and which sensors are to be deactivated at which times.

The switch circuitry 328 can also connect the electrodes 106a and 106b to the battery charging circuitry 340, e.g., when the sensor pod is resting in or on a charging unit 500, as discussed in additional detail in U.S. patent application Ser. No. 14/661,869, filed Apr. 31, 2015. Alternatively, the sensor pod 100 can include dedicated electrical contacts that are permanently connected to the battery charging unit 340.

As explained above in the discussion of FIGS. 2A and 2B, the sensor pod 100 can be inserting into an opening 204 in a wrist band 202, or some other band or strap, such as a headband, arm band or some other user wearable band, strap or device. As also noted above, the sensor pod 100 can alternatively be placed into a pocket within a sock or tight fitting shirt (e.g., a bicycle shirt) or other article of apparel or clothing that includes a pocket for the sensor pod 100. Such a pocket can include an opening that enables the backside of the sensor pod 100, which includes windows for the PPG sensor (and/or other optical sensor(s)), electrodes and/or other sensor elements, to contact the wearer's skin to thereby enable the sensor(s) to operate properly. Such an opening can also enable the groove 112 in the sensor pod 100 to be snapped into a correct position and held in place against a user's skin. The sensor pod 100 can alternatively be placed in an opening, slot and/or pocket in a headband, helmet (e.g., a bicycle, motorcycle, skateboard, football, baseball, hockey, snowboard or ski helmet) or other headwear (e.g., a beanie, a baseball cap or any other type of hat). The sensor pod 100 may alternatively be placed an opening, slot and/or pocket in a pair of glasses or a head mounted display (HMD) that positions the back surface 114 of the sensor pod 100 against a user's temple. Exemplary details of how the sensor pod 100 can be selectively attached to an article of apparel or clothing as discussed in U.S. patent application Ser. No. 14/661,831, filed Apr. 31, 2015.

Figure 4:
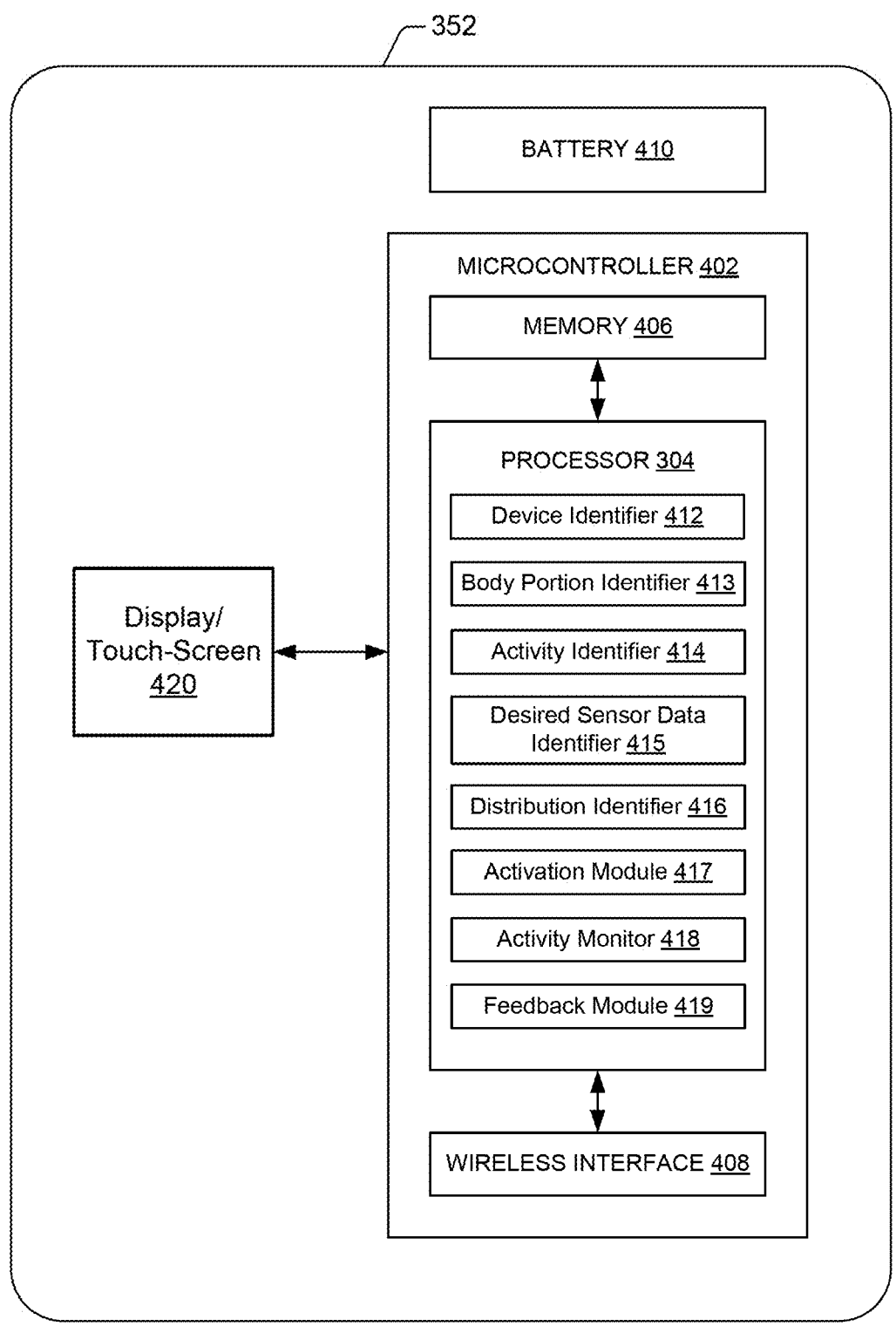
FIG. 4 depicts an example block diagram of the electrical components of a base station that is capable of wirelessly communicating with one or more of physiological sensor pod introduced in FIGS. 1A, 1B and 1C, for which additional details were described with reference to FIG. 3.

FIG. 4 depicts an example block diagram of the electrical components of a base station 352 that is capable of wirelessly communicating with one or more of the physiological sensor pods 100 introduced in FIGS. 1A, 1B and 1C, and for which additional details were described above with reference to FIG. 3. As mentioned above, the base station 352 can be a mobile computing device or any other computing device that includes wireless communication capabilities. For example, the base station 352 can be a smartphone, such as, but not limited to, an iPhone™, a Blackberry™, an Andriod™-based or a Windows™-based smartphone. The base station 352 can alternatively be a tablet computing device, such as, but not limited to, an iPad™, an Andriod'-based or a Windows™-based tablet. These are just example, which are not intended to be all encompassing.

Referring to FIG. 4, the base station 352 is shown as including a microcontroller 402 that includes a processor 404, memory 406 and a wireless interface 408. It is also possible that the memory 406 and wireless interface 408, or portions thereof, are external the microcontroller 402. The base station 352 is also shown as including a display 420 (which may or may not be a touch screen display) and a battery 410. The battery 410 can be used to power the various other components of the base station 352. Where the base station 352 is not a mobile device, the battery 410 may be eliminated and the base station 352 may be plugged into a power supply, or the like. While not specifically shown, the base station 352 may also include other components, such as a bus that enables the various components of the base station to communicate with one another. Where the base station 352 includes a battery 410, the base station 352 may also include a battery charging circuit, not specifically shown in FIG. 4. The base station 352 may also include a speaker and/or a microphone. Additionally, the base station 352, where it is a smart phone or tablet computing device, may also include a camera, an accelerometer, a magnetometer, a gyroscope and/or the like.

The display 420, which many or not be a touch screen type of display, can be used as a graphical user interface (GUI) to visually display items (e.g., images, options, instructions, etc.) to a user and accept inputs from a user. Further, the base station 352 can include additional elements, such as keys, buttons, a track-pad, a trackball, or the like, that accept inputs from a user.

The memory 406 can be used to store software and/or firmware that controls the base station 352, as well to store data transmitted to the base station 352 from one or more physiologic sensor pods 100, or more generally, user-wearable devices, but is not limited thereto. Various different types of memory, including non-volatile and volatile memory can be included in the base station 352. The base station 352 can also include a drive unit, e.g., a hard drive, but not limited thereto, that can also be used to store software that controls the base station 352, but is not limited thereto. The memory 418 (and/or a drive unit) can include a machine readable medium on which is stored one or more sets of executable instructions (e.g., apps) embodying one or more of the methodologies and/or functions described herein. In place of the drive unit, or in addition to the drive unit, the mobile computing device can include a solid-state storage device, such as those comprising flash memory or any form of non-volatile memory. The term "machine-readable medium" as used herein should be taken to include all forms of storage media, either as a single medium or multiple media, in all forms; e.g., a centralized or distributed database and/or associated caches and servers; one or more storage devices, such as storage drives (including e.g., magnetic and optical drives and storage mechanisms), and one or more instances of memory devices or modules (whether main memory, cache storage either internal or external to a processor, or buffers. The term "machine-readable medium" or "computer-readable medium" shall be taken to include any tangible non-transitory medium which is capable of storing or encoding a sequence of instructions for execution by the machine and that cause the machine to perform any one of the methodologies. The term "non-transitory medium" expressly includes all forms of storage drives (optical, magnetic, etc.) and all forms of memory devices (e.g., DRAM, Flash (of all storage designs), SRAM, MRAM, phase change, etc., as well as all other structures designed to store information of any type for later retrieval.

The wireless interface 408 can wirelessly communicate with one or more of the physiologic sensor pods 100, or more generally, with one or more user-wearable devices. The wireless interface 408 can also wirelessly communication with other computing devices having wireless communication capabilities. The wireless interface 408, and more generally the base station 352, can communicate with one or more user-wearable devices using various different protocols and technologies, such as, but not limited to, Bluetooth™, Wi-Fi™, ZigBee™ or ultrawideband (UWB) communication. In accordance with an embodiment, the wireless interface 408 comprises telemetry circuitry that include a radio frequency (RF) transceiver electrically connected to an antenna (not shown), e.g., by a coaxial cable or other transmission line. Such an RF transceiver can include, e.g., any well-known circuitry for transmitting and receiving RF signals via an antenna to and from an RF transceiver of a user-wearable device (e.g., a sensor pod 100).

Still referring to FIG. 4, the base station 352 is shown as including various modules, including a device identifier module 412, a body portion identifier module 413, an activity identifier module 414, a desired sensor data module 415, a distribution identifier module 416, an activation module 417, an activity monitor module 418 and a feedback module 419. The various modules may communicate with one another, as will be explained below. Each of these modules 412, 413, 414, 415, 416, 417, 418 and 419 can be implemented using software, firmware and/or hardware. It is also possible that some of these detectors and trackers are implemented using software and/or firmware, with others implemented using hardware. Other variations are also possible. In accordance with a specific embodiments, each of these modules 412, 413, 414, 415, 416, 417, 418, 419 is implemented using software code that is stored in the memory 406 and is executed by the processor 404. The memory 406 is an example of a tangible computer-readable storage apparatus or memory having computer-readable software embodied thereon for programming a processor (e.g., 404) to perform a method. For example, non-volatile memory can be used. Volatile memory such as a working memory of the processor 404 can also be used. The computer-readable storage apparatus may be non-transitory and exclude a propagating signal.

The device identifier module 412, which can also be referred to simply as the device identifier 412, is adapted to identify each of a plurality of sensor pods 100 (or more generally, user-wearable devices) that are attached to a user's body. For example, referring briefly to FIG. 5, a person 500 (which can also be referred to as a user 500) is shown as wearing six sensor pods 100 (or more generally, six user-wearable devices) labeled 100a, 100b, 100c, 100d, 100e and 100f. More specifically, the sensor pod 100a is positioned against the user's chest, the sensor pod 100b is strapped to the user's right wrist, the sensor pod 100c is strapped to the user's left wrist, the sensor pod 100d is strapped to the user's right ankle, the sensor pod 100e is strapped to the user's left ankle, and the sensor pod 100f is strapped to the user's forehead. The user 500 is also shown as having a base station 352 strapped to their arm. More or less sensor pods 100, or more generally, user-wearable devices, can be worn by a user.

Figure 5:
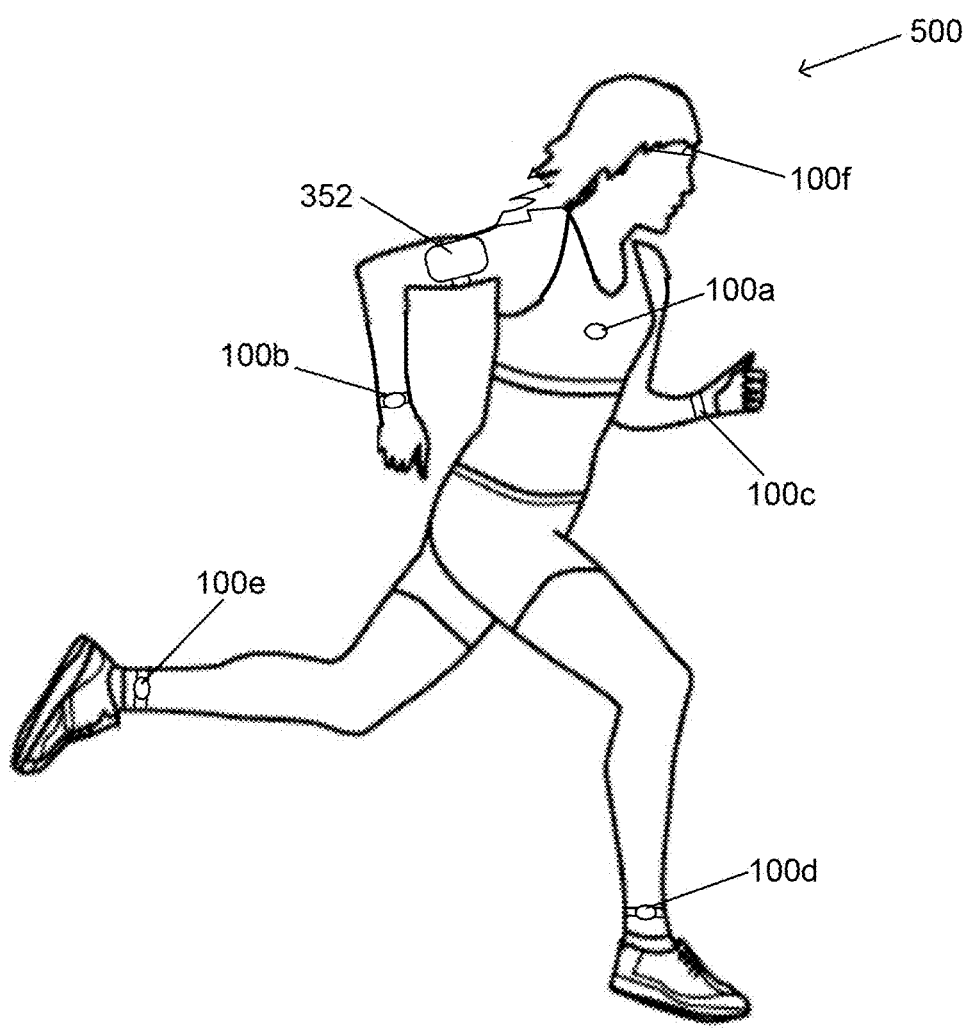
FIG. 5 illustrates a system according to an embodiment of the present technology.

More generally, FIG. 5 illustrates a system including a plurality user-wearable devices, each of which is worn on a separate portion of a user's body, each of which is battery powered, each of which includes a plurality of sensors, and each of which is adapted to wirelessly communicate with a common base station. In FIG. 5, the user-wearable devices are assumed to be multiple sensor pods 100, individually labeled 100a, 100b, 100c, 100d, 100e and 100f, each of which can be referred to as a sensor pod 100, or more generally as a user-wearable device 100. The user-wearable device 100a is shown is being placed against a user's chest, either by attaching it to a tight shirt or using a chest strap. The user-wearable devices 100b and 100c are shown as being attached to (or more generally, worn on) the user's left and right wrists, respectively, e.g., using wrist-bands. The user-wearable devices 100d and 100e are shown as being attached to the user's left and right ankles, respectively, e.g., using ankle bands. Additionally, the user-wearable device 100f is shown as being strapped to the user's forehead, e.g., using a headband. Further, the base station 352, which can be, e.g., a smart phone, is shown as being strapped to the user's upper arm. For much of the following discussion, it is assumed that each of the user-wearable devices are the same as one another, i.e., are multiple interchangeable units of the same product, however, in alternative embodiments that need not be the case. While the system in FIG. 5 is shown as including six user-wearable devices 100 and a base station 352, the system can alternatively include more or less user-wearable devices 100, so long as the system includes at least two user-wearable devices 100 and a base station 352.

In accordance with certain embodiments of the present technology, each of the user-wearable devices 100 is capable of using one or more of its sensors to measure or otherwise obtain activity and/or physiological data and wirelessly transmit such data to the base station 352. In such embodiments, the base station 352 can function as a data aggregation device that can be used for various different purposes, some of which are discussed below. For example, the base station 352 can be used to identify an activity in which the user is engaged, and based on such activity, can monitor and track physiological parameters of the user and/or athletic performance parameters of the user. The base station 352 can also distribute sensing responsibilities among the sensors of the user-wearable devices 100, e.g., so that each of the devices 100 provides the base station 352 with appropriate data that enables the base station 352 to perform its analysis, as well as for power management reasons. For example, assume that the battery life of each of the devices 100, after a full charge, would only be five hours if every sensor of every device 100 was operating at all times. Assuming that each of the devices 100 included the same sensors and collected the same data, this would result in a significant amount of redundant data being provided to the base station 352. Additionally, some of the data collected by some of the devices 100 may be inaccurate or otherwise not useful. For a specific example, an ECG signal obtained by a user-wearable device attached to a user's ankle would be an inaccurate (or nonexistent) since the user's chest cavity, in which their heart is located, would not be located between the electrodes (e.g., 106a and 106b) that attempt to obtain the ECG signal. Accordingly, for both data accuracy and battery power conservation reasons, embodiments of the present technology are used to selectively enable and disable certain sensors and/or other circuitry of the user-wearable devices 100. For example, the ECG circuit (e.g., 329) of user-wearable device(s) (e.g., 100e and/or 100d) being worn on a user's ankle may be purposely disabled to conserver battery power, as well as to avoid providing inaccurate ECG data to the base station 352.

Referring again to FIG. 4, the device identifier module 412 can identify each of the sensor pods 100 (or more generally, user-wearable devices) based on manual inputs to the base station 352 entered by a user. For example, each of the sensor pods 100 can have a unique identifier (ID) printed on its housing 102, and the base station 352 can present, via the display 420, a device identifier screen which enables the user to manually specify how many sensor pods 100 they are wearing, and enter the IDs of the sensor pods 100. It is also possible that multiple screens be presented to the user to enable them to enter such information. Alternatively, or additionally, the base station 352 can identify each of the sensor pods 100 based on information, including sensor pod IDs, wirelessly transmitted by the sensor pods 100 to the base station 352. The sensor pods 100 may transmit such information in response to wireless inquiry messages transmitted by the base station 352, and/or the sensor pods 100 can periodically transmit such information.

Still referring to FIG. 4, the body portion identifier module 413, which can also be referred to simply as the body portion identifier 413, is adapted to identify, for each of the sensor pods 100 (or more generally, for each of the user-wearable devices), the portion of the user's body to which the sensor pod 100 is attached. Such information can be manually entered into the base station 352 by a user. For example, the same screen(s) that enabled the user to specify how many sensor pods 100 they are wearing, and enter the IDs of the sensor pods 100, can also enable the user to specify where each of the sensor pods is being worn. Such screen(s) can be pictorial and/or textual. Alternatively, or additionally, the base station 352 can identify each of the sensor pods 100 based on sensor data wirelessly transmitted by the sensor pods 100 to the base station 352. The sensor pods 100 may transmit such sensor data in response to wireless inquiry messages transmitted by the base station, and/or the sensor pods 100 can periodically transmit such sensor data. For example, if a sensor pod 100 transmits actual ECG data obtaining using the electrodes (e.g., 106a and 106b) on the bottom or back surface of the housing 114 of the sensor pod 100, then the body portion identifier 413 can determine that the particular sensor pod 100 is positioned on and against the user's chest. Motion data, obtained using one or more types of motions sensors 342 of the sensor pods 100, can be used by the body portion identifier 413 to determine whether a sensor pod 100 is located on an arm, leg or forehead, because the expected motion for each such body positions will be unique to the body position. Motion data may also be used to distinguish between a sensor pod 100 being located on a user's right wrist or left wrist, and distinguish between a sensor pod 100 being located on a user's right angle or left ankle. Alternatively, or additionally, a user may manually enter such information into the base station 352. In accordance with an embodiment, the body portion identifier 413 uses sensor data obtained from multiple sensor pods 100 to determine, the best it can, where each sensor pod is being worn, and such information is presented to the user on the display 420, and the user is provided with the ability to confirm the locations of the sensor pods are correct, or to correct any locations that are inaccurate.

Still referring to FIG. 4, the activity identifier module 414, which can also be referred to simply as the activity identifier 414, is adapted to identify an activity in which the user is engaged. Exemplary activities in which the user may be engaged include, but are not limited to, walking, running, biking, swimming, playing basketball, playing soccer, playing tennis, playing football, skiing, snowboarding, just to name a few. In an embodiment, the activity detector 319 can cause a list of possible activities in which a user may be engaged to be displayed on the display 420, from which the user can manually select the activity, e.g., using a touch screen or other user interface of the base station 352. Additionally, or alternatively, the activity identifier 414 can identify the activity in which a user is engaged based on sensor date wirelessly transmitted by the sensor pods 100 to the base station 352. The sensor pods 100 may transmit such sensor data in response to wireless inquiry messages transmitted by the base station, and/or the sensor pods 100 can periodically transmit such sensor data. For example, the activity identifier 414 can use motion data, obtained by the motion sensors 342 of the sensor pods 100, to identify an activity in which a user is engaged since different types of activities will have different motion signatures. For a more specific example, while the type of motion when a user is walking versus running will be similar, the rate of such motion will be distinct. For another example, the motion of a user's wrist when playing basketball will be quite different than the motion of a user's wrist when walking or running Swimming, biking, etc., similarly have unique motion signatures that can enable the activity identifier 414 to identify an activity in which a user is engaged. In accordance with an embodiment, the activity identifier 414 uses sensor (e.g., motion) data obtained from multiple sensor pods 100 to determine, the best it can, the activity in which the user is engaged, and such information is presented to the user on the display 420, and the user is provided with the ability to confirm the identified activity is correct, or to correct the activity if it is inaccurately identified.

The desired sensor data identifier module 415, which can also be referred to simply as the desired sensor data identifier 415, is adapted to identify, in dependence on the activity in which the user is engaged and the portions of the user's body on which the sensor pods 100 are being worn, multiple types of sensor data are to be sensed, using the sensors of the sensor pods 100, to enable software and/or firmware within the base station 352 to track metrics relevant to the activity in which the user is engaged. For example, where a user is running, metrics relevant to running can include heart rate (HR), heart rate variability (HRV), the speed or pace at which the user is running, the cadence at which the user is running, and the position of the user's head, just to name a few. ECG sensor data (corresponding to an obtained ECG signal) or PPG sensor data (corresponding to an obtained PPG signal) can be used to determine HR and/or HRV. Appropriate motion data can be used to determine the speed or pace at which the user is running, the cadence at which the user is running, and the position of the user's head. Where a user is not wearing a sensor pod on specific portions of their body from which it would be useful to sense data, the base station 352 may recommend to the user that they utilize one or more additional sensor pod(s). Nevertheless, the base station 352 can be programmed to do the best it can with what data it is capable of obtaining from sensor pods 100 attached to a user. For example, while it may be beneficial to track the position and/or motion of a user's head for certain types of activities, such as running or swimming, if the user is not wearing a sensor pod against their forehead, then the base station 352 can still obtain other relevant sensor data for the activity in which the user is engaged. In certain embodiments, the desired sensor data identifier 415 can determine that sensor signal data, such as ECG signal data and/or PPG signal data, is desired. Alternatively, the desired sensor data identifier 415 may determine that data determined by base station(s) from sensor signal data, e.g., HR and/or HRV data, is desired. More generally, the desired sensor data identifier 415 can determine whether certain parameters, such as HR and HRV, should be determined by one or more sensor pods, or should be determined by the base station based on sensor signal data received from one or more sensor pods.

The distribution identifier module 416, which can also be referred to simply as the distribution identifier 416, is adapted to determine, in dependence on the activity in which the user is engaged and the portions of the user's body on which the sensor pods 100 (and more generally, user wearable devices) are being worn, how to distribute sensing responsibilities for the multiple types of sensor data (identified by the desired sensor data identifier 415) among the sensors of the plurality of sensor pods 100 being worn by the user. For example, as just explained above, where a user is running, the desired sensor data identifier 415 may identify, as sensor data relevant to running, sensor data that enables the determination of a user's heart rate (HR), the user's heart rate variability (HRV), the speed or pace at which the user is running, the cadence at which the user is running, and the position of the user's head. The distribution identifier 416 may then identify which sensors should be used to obtain such sensor data. In certain embodiments, the distribution identifier 416 is adapted to distribute the sensing responsibilities, for the multiple types of sensor data, among the sensors of the plurality of sensor pods (and more generally, the user-wearable devices) in order to increase how long each of the sensor pods can operate between battery charges or replacements, compared to if each sensor pod (and more generally, each user-wearable device) sensed all of the sensor data.

For example, referring again to FIG. 5, the user 500 is shown as wearing six sensor pods 100a, 100b, 100c, 100d, 100e, 100f, wherein each of the sensor pods 100 includes the same sensors, examples of which were described above with reference to FIG. 3. The desired sensor data identifier 415 may determine that an ECG or PPG signal should be obtained in order for the user's HR and/or HRV to be determined. It would be redundant, and wasteful in terms of battery power consumption, for every one of the six sensor pods 100 to obtain both an ECG signal and a PPG signal, when in fact a single ECG or PPG signal obtained from a single one of the sensor pods 100 would suffice to determine the user's HR and/or HRV. In such a situation, the distribution identifier 416 may specify that only one of the sensor pods 100 is to obtain either an ECG signal or a PPG signal. The specific sensor pod 100 selected to obtaining the ECG or PPG signal may be the one most likely to obtain the most accurate and/or clean signal given the activity in which the user is engaged and the locations of the sensor pods. For example, the sensor pod 100a, which is positioned against the user's chest, is closest to the user's heart and is likely subjected to the least motion artifacts, and thus, may be chosen by the distribution identifier 416 as the single sensor pod that is to obtain an ECG signal or PPG signal. The distribution identifier 416 may also select whether to obtain an ECG signal or a PPG signal, as many metrics, such as HR and HRV, can be determined based on either type of sensed signal. In contrast, where the parameter identifier 415 determines that measures of blood pressure are to be obtained, the distribution identifier 416 may specify that one sensor pod (e.g., the sensor pod 100a against the user's chase) is to obtain an ECG signal and another sensor pod (e.g., the sensor pod 100b on the user's right wrist) is to obtain a PPG signal, so the measures of pulse wave velocity (PWV) can be determined, and used to estimate blood pressure.

For another example, motion data from any one of the sensor pods 100 attached to (or more generally, worn on) the user's wrists and ankles (i.e., 100b, 100c, 100d and 100e) may be sufficient to obtain the speed or pace at which the user is running, as well as the cadence at which the user is running. Accordingly, the distribution identifier 416 may specify that only one of the sensor pods 100b, 100c, 100d and 100e is to obtain motion data. It is also possible that the distribution identifier 416 changes over time the one of the sensor pods 100b, 100c, 100d and 100e that is responsible for obtaining motion data, so as to not run down the battery of any single one of the sensor pods 100. For example, the distribution identifier 416 can determine a schedule for the sensor pods 100b, 100c, 100d and 100e to obtain motion data, such that no single one of those sensor pods obtains motion data for more than a specified consecutive amount of time (e.g., 5 minutes). These are just a few examples, which are not intended to be all encompassing.

Referring again to FIG. 4, the activation module 417 is adapted to selectively activate and deactivate individual sensors of each of the sensor pods 100 (or more generally, the user-wearable devices) in dependence on a determination, by the distribution identifier 416, of how to distribute the sensing responsibilities for the multiple types of sensor data. In accordance with certain embodiments, the activation module 417 causes the wireless interface 408 to transmit signals to the various sensor pods 100 that specify, to each of the sensor pods, which of its sensors are to be activated and which of its sensors are to be deactivated (also referred to as disabled) at any given time. More generally, the activation module 417 can inform each of the sensor pods of which type(s) of sensor data the sensor pod is responsible for obtaining and transmitting to the base station 352.

The activity monitor module 418, which can also be referred to simply as the activity monitor 418, is adapted to use sensor data received from the sensor pods 100 to track one or more metrics relevant to the activity in which the user is engaged. For example, where a sensor pod 100 transmits data indicative of an ECG signal or PPG signal (which can also be referred to as ECG signal data or ECG data, or PPG signal data or PPG data) to the base station 352, the activity monitor 418 may determine HR and/or HRV based therein. Accordingly, the activity monitor 418 can be thought of as including many submodules, e.g., a HR detector module and an HRV detector module. It should also be noted that a sensor pod itself may determine HR and/or HRV based on an ECG or PPG signal it obtains, in which case, the sensor pod can transmit HR and/or HRV data to the base station 352, which would eliminate the need for the base station 352, or the activity monitor 418 thereof, to determine HR and/or HRV. For another example, where one or more sensor pods 100 transmit motion data to the base station 352, the activity monitor 418 can determine, based on the motion data, the speed or pace at which a user is running, as well as the cadence at which the user is running. It should also be noted that a sensor pod itself, if appropriately configured, may determine the speed at which a user is running, and/or the like, in which case, the sensor pod can transmit speed data to the base station 352, which would eliminate the need for the base station 352, or the activity monitor 418 thereof, to determine the speed at which the user is running, and/or the like.

The feedback module 419 is adapted to provide feedback to the user in dependence on the tracked one or more metrics relevant to the activity in which the user is engaged. The feedback can be indicative of the user's performance. Alternatively, or additionally, the feedback can be indicative of the user's progress towards a goal. Additionally, or alternatively, the feedback can include advice for improving the user's performance. Such feedback can be displayed on the display of 420 of the base station 352, and/or can be auditory, in which case it is provided using a speaker of the base station 352. For an example, the feedback module 419 may inform a user of how far they have run, the average speed at which they have run, how much further they need to run to reach a predetermined goal, whether they should increase or reduce their speed, and/or the like. For another example, the feedback module 419 may instruct a user to increase (or decrease) their heart rate.

In the FIGS. and the above description, the sensor pod 100 was shown as and described as having an oval or elliptical circumferential shape. In alternative embodiments the sensor pod 100 can have alternative circumferential shapes, such as circular, rectangular, or square, but not limited thereto.

Figure 6:
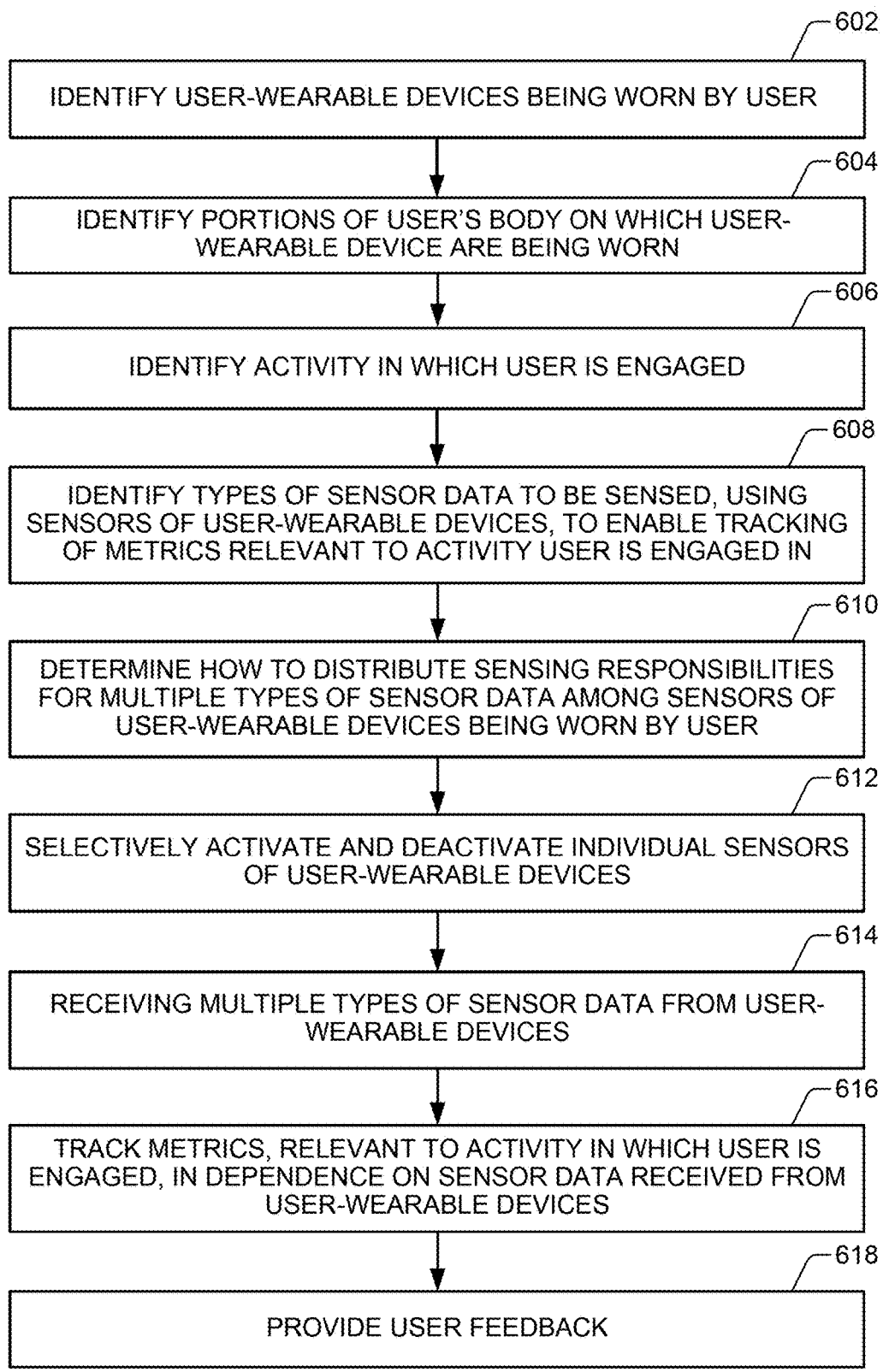
FIG. 6 is a high level flow diagram that is used to summarize methods according to various embodiments of the present technology.

FIG. 6 will now be used to describe methods for use by a system including a plurality user-wearable devices, each of which is worn on a separate portion of a user's body, each of which is battery powered, each of which includes a plurality of sensors, and each of which is adapted to wirelessly communicate with a common base station. In certain embodiments, all of the steps described with reference to FIG. 6 are performed by the base station of the system, which as mentioned above, can be a mobile computing device (e.g., smart phone, a tablet computer, a personal data assistant (PDA) or a laptop computer), a desktop computer, or some other computing device that is capable of performing wireless communication. In certain embodiments, each of the user-wearable devices includes the same sensors as the other user-wearable devices.

Referring to FIG. 6, step 602 involves identifying each of a plurality of user-wearable devices that are being worn by a user, wherein each of the user-wearable devices is battery powered, includes a plurality of sensors, is adapted to perform wirelessly communication, and is being worn on a separate portion of the user's body. Each of the user-wearable devices can be, e.g., one of the sensor pods 100 described above, but is not limited thereto. Step 602 can be automatically performed by a base station (e.g., 352), in wireless communication with the user-wearable devices, in response to the base station receiving wireless signals including unique identifiers from the user-wearable devices. Alternatively, step 602 can be performed by a base station (e.g., 352), in wireless communication with the user-wearable devices, in response to one or more user inputs accepted by the base station. In certain embodiments, step 602 is performed by the device identifier (e.g., 412) of a base station.

Step 604 involves, for each of the plurality of user-wearable devices, identifying a portion of the user's body on the user-wearable device is being worn. Step 604 can be automatically performed by a base station (e.g., 352), in wireless communication with the user-wearable devices, in response to the base station receiving wireless signals including sensor data from the user-wearable devices. Alternatively, step 604 can be performed by a base station (e.g., 352), in wireless communication with the user-wearable devices, in response to one or more user inputs accepted by the base station. In certain embodiments, step 604 is performed by a body portion identifier (e.g., 413) of a base station.

Step 606 involves identifying an activity in which the user is engaged. Step 606 can be automatically performed by a base station (e.g., 352), in wireless communication with the user-wearable devices, in response to the base station receiving wireless signals including sensor data emitted by the user-wearable devices. In such an embodiment, the user-wearable devices (e.g., 100) may initially activate all of their sensors (e.g., in response to being instructed to by the base station, or by default) and collect all of the sensor data they are capable of collecting, and the user-wearable devices may transmit such sensor data to a base station. The user-wearable devices can thereafter deactivate their sensors by default, or in response to instructions received from the base station. At a later point in time, e.g., corresponding to step 612, each of the user-wearable devices may selectively activate and deactivate specific sensor of the device in response to instructions received from the base station. Alternatively, step 606 is performed by a base station (e.g., 352), in wireless communication with the user-wearable devices, in response to user inputs accepted by the base station. In certain embodiments, step 606 is performed by an activity identifier (e.g., 414) of a base station.

Step 608 involves identifying, in dependence on the activity in which the user is engaged and the portions of the user's body on which the user wearable devices are being worn, multiple types of sensor data that are to be sensed, using the sensors of the user-wearable devices, to enable tracking of one or more metrics relevant to the activity in which the user is engaged. In certain embodiments, step 608 is performed by a desired sensor data identifier (e.g., 415) of a base station.

Step 610 involves determining, in dependence on the activity in which the user is engaged and the portions of the user's body on which the user wearable devices are being worn, how to distribute sensing responsibilities for the multiple types of sensor data among the sensors of the plurality of user-wearable devices being worn by the user. In certain embodiments, step 610 includes distributing the sensing responsibilities for the multiple types of sensor data among the sensors of the plurality of user-wearable devices in order to increase how long each of the user-wearable devices can operate between battery charges or replacements, compared to if each user-wearable device sensed all of the multiple types of sensor data. In certain embodiments, step 610 is performed by a distribution identifier (e.g., 416) of a base station.

Step 612 involves selectively activating and deactivating individual sensors of each of the user-wearable devices in dependence on results of step 610. In certain embodiments, step 612 is performed by an activation module (e.g., 417) of a base station.

Step 614 involves receiving the multiple types of sensor data from the user-wearable devices. In certain embodiments, step 614 is performed by a wireless interface (e.g., 408) of a base station. One type of sensor data may be received from a first one of the user-wearable devices, while another type of sensor data is received from another one of the user-wearable devices, etc. The particular user-wearable device from which particular sensor data is obtained will depend on the results of steps 610 and 612.

Step 616 involves tracking the one or more metrics, relevant to the activity in which the user is engaged, in dependence on sensor data received from the user-wearable devices. In certain embodiments, step 616 is performed by an activity monitor (e.g., 418) of a base station.

Step 618 involves providing user feedback in dependence on the tracked metrics relevant to the activity in which the user is engaged, wherein the user feedback is indicative of the user's performance, indicative of the user's progress towards a goal, and/or includes advice for improving the user's performance. In certain embodiments, step 618 is performed by a feedback module (e.g., 419) of a base station.

Further details of the methods described above with reference to FIG. 6 can be appreciated from the above discussion of FIGS. 1A-5.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto. While various embodiments have been described above, it should be understood that they have been presented by way of example, and not limitation. It will be apparent to persons skilled in the relevant art that various changes in form and detail can be made therein without departing from the spirit and scope of the invention. The breadth and scope of the present invention should not be limited by any of the above-described exemplary embodiments, but should be defined only in accordance with the following claims and their equivalents.

What is claimed is:

1. A method, comprising:
   (a) identifying each of a plurality of user-wearable devices that are being worn by a user, wherein each of the user-wearable devices is battery powered, includes a plurality of sensors, is adapted to perform wireless communication, and is being worn on a separate portion of the user's body;
   (b) for each of the plurality of user-wearable devices, identifying a portion of the user's body on which the user-wearable device is being worn;
   (c) identifying an activity in which the user is engaged;
   (d) identifying, in dependence on the activity in which the user is engaged and the portions of the user's body on which the user wearable devices are being worn, multiple types of sensor data that are to be sensed, using the sensors of the user-wearable devices, to enable tracking of one or more metrics relevant to the activity in which the user is engaged;
   (e) determining, in dependence on the activity in which the user is engaged and the portions of the user's body on which the user wearable devices are being worn, how to distribute sensing responsibilities for the multiple types of sensor data among the sensors of the plurality of user-wearable devices being worn by the user,
   wherein when a same identified type of sensor data that is to be sensed is obtainable from a same type of sensor of more than one of the user-wearable devices, the determining how to distribute the sensing responsibilities includes determining a schedule that changes over time how the sensing responsibilities are distributed among the sensors of the plurality of user-wearable devices being worn by the user in order to increase how long each of the user-wearable devices can operate between battery charges or replacements, compared to if distribution of the responsibilities among the sensors of the plurality of user-wearable devices being worn by the user remained unchanged after an initial distribution was determined; and
   (f) selectively activating and deactivating individual sensors of each of the user-wearable devices in dependence on results of step (e).

2. The method of claim 1, wherein step (e) includes distributing the sensing responsibilities for the multiple types of sensor data among the sensors of the plurality of user-wearable devices in order to increase how long each of the user-wearable devices can operate between battery charges or replacements, compared to if each user-wearable device sensed all of the sensor data.

3. The method of claim 1, further comprising:
   (g) receiving the multiple types of sensor data from the user-wearable devices; and
   (h) tracking the one or more metrics, relevant to the activity in which the user is engaged, in dependence on sensor data received from the user-wearable devices.

4. The method of claim 3, further comprising:
   (i) providing user feedback in dependence on the tracked one or more metrics relevant to the activity in which the user is engaged, wherein the user feedback is indicative of the user's performance, indicative of the user's progress towards a goal, and/or includes advice for improving the user's performance.

5. The method of claim 1, wherein:
   step (a) is automatically performed by a base station, in wireless communication with the user-wearable devices, in response to the base station receiving wireless signals including unique identifiers from the user-wearable devices; or step (a) is performed by a base station, in wireless communication with the user-wearable devices, in response to one or more user inputs accepted by the base station.

6. The method of claim 1, wherein step (b) is automatically performed by a base station, in wireless communication with the user-wearable devices, in response to the base station receiving wireless signals including sensor data from the user-wearable devices.

7. The method of claim 1, wherein step (b) is performed by a base station, in wireless communication with the user-wearable devices, in response to one or more user inputs accepted by the base station.

8. The method of claim 1, wherein step (c) is automatically performed by a base station, in wireless communication with the user-wearable devices, in response to the base station receiving wireless signals including sensor data from the user-wearable devices.

9. The method of claim 1, wherein step (c) is performed by a base station, in wireless communication with the user-wearable devices, in response to user inputs accepted by the base station.

10. The method of claim 1, wherein each of the user-wearable devices includes the same plurality of sensors as the other user-wearable device(s).

11. The method of claim 1, wherein when a same identified type of sensor data that is to be sensed is obtainable from a same type of sensor of more than one of the user-wearable devices, the schedule that is determined ensures that no individual one of the sensors of the same type obtains the identified type of sensor data for more than a specified consecutive amount of time.

12. A base station adapted to communicate with a plurality user-wearable devices, each of which includes a battery that powers the user-wearable device, each of which includes a plurality of sensors, each of which includes a wireless interface that is adapted to wirelessly communicate with the base station, and each of which is intended to worn on a separate portion of a user's body, the base station comprising:

a wireless interface adapted to transmit and receive wireless signals, wherein the wireless interface enables the base station to wireless communicate with the plurality of the user-wearable devices;

a device identifier module adapted to identify each of the plurality of user-wearable devices that are being worn by the user;

a body portion identifier module adapted to identify, for each of the plurality of user-wearable devices, the portion of the user's body on which the user-wearable device is being worn;

an activity identifier module adapted to identify an activity in which the user is engaged;

a desired sensor data identifier module adapted to identify, in dependence on the activity in which the user is engaged and the portions of the user's body on which the user wearable devices are being worn, multiple types of sensor data that are to be sensed, using the sensors of the user-wearable devices, to enable the base station to track metrics relevant to the activity in which the user is engaged;

a distribution identifier module adapted to determine, in dependence on the activity in which the user is engaged and the portions of the user's body on which the user wearable devices are being worn, how to distribute sensing responsibilities for the multiple types of sensor data among the sensors of the plurality of user-wearable devices being worn by the user; and an activation module adapted to selectively activate and deactivate individual sensors of each of the user-wearable devices in dependence on a determination, by the distribution identifier module, of how to distribute the sensing responsibilities for the multiple types of sensor data;

wherein when the distribution identifier module determines that a same identified type of sensor data that is to be sensed is obtainable from a same type of sensor of more than one of the user-wearable devices, the distribution identifier module is adapted to determine a schedule that changes over time how the sensing responsibilities are distributed among the sensors of the plurality of user-wearable devices being worn by the user in order to increase how long each of the user-wearable devices can operate between battery charges or replacements, compared to if distribution of the responsibilities among the sensors of the plurality of user-wearable devices being worn by the user remained unchanged after an initial distribution was determined.

13. The base station of claim 12, wherein the distribution identifier module is adapted to distribute the sensing responsibilities for the multiple types of sensor data among the sensors of the plurality of user-wearable devices in order to increase how long each of the user-wearable devices can operate between battery charges or replacements, compared to if each user-wearable device sensed all of the multiple types of sensor data.

14. The base station of claim 12, further comprising:
an activity monitor module adapted to use the multiple types of sensor data received from the user-wearable devices to track the one or more metrics relevant to the activity in which the user is engaged.

15. The base station of claim 12, further comprising:
a feedback module adapted to provide feedback to the user in dependence on the tracked one or more metrics relevant to the activity in which the user is engaged, the feedback being indicative of the user's performance, being indicative of the user's progress towards a goal, and/or including advice for improving the user's performance.

16. The base station of claim 12, wherein the device identifier module is adapted to identify each of the plurality of user-wearable devices that are being worn by the user in dependence on unique identifiers included in wireless signals, emitted by the user-wearable devices, that are received by the wireless interface of the base station.

17. The base station of claim 12, wherein the device identifier module is adapted to identify each of the plurality of user-wearable devices that are being worn by the user in dependence on one or more user inputs accepted by a user interface of the base station.

18. The base station of claim 12, wherein the body portion identifier module is adapted to identify, for each of the plurality of user-wearable devices, the portion of the user's body on which the user-wearable device is being worn in dependence on sensor data included in wireless signals, emitted by the user-wearable devices, that are received by the wireless interface of the base station.

19. The base station of claim 12, wherein the body portion identifier module is adapted to identify, for each of the plurality of user-wearable devices, the portion of the user's body on which the user-wearable device is being worn in dependence on one or more user inputs accepted by a user interface of the base station.

20. The base station of claim 12, wherein the activity identifier module is adapted to identify an activity in which the user is engaged in dependence on sensor data included in wireless signals, emitted by the user-wearable devices, that are received by the wireless interface of the base station.

21. The base station of claim 12, wherein the activity identifier module is adapted to identify an activity in which the user is engaged in dependence on one or more user inputs accepted by a user interface of the base station.

22. The base station of claim 12, wherein when the distribution identifier module determines that a same identified type of sensor data that is to be sensed is obtainable from a same type of sensor of more than one of the user-wearable devices, the schedule that is determined by the distribution identifier module ensures that no individual one of the sensors of the same type obtains the identified type of sensor data for more than a specified consecutive amount of time.

23. A system comprising:
   a base station;
   a plurality user-wearable devices, each of which includes a battery that powers the user-wearable device, each of which includes a plurality of sensors, each of which includes a wireless interface that is adapted to wirelessly communicate with the base station, and each of which is intended to worn on a separate portion of a user's body;
   wherein the base station is configured to
      identify each of the plurality of user-wearable devices that are being worn by a user;
      for each of the plurality of user-wearable devices, identify a portion of the user's body on which the user-wearable device is being worn;
      identify an activity in which the user is engaged;
      identify, in dependence on the activity in which the user is engaged and the portions of the user's body on which the user wearable devices are being worn, multiple types of sensor data that are to be sensed, using the sensors of the user-wearable devices, to enable tracking of one or more metrics relevant to the activity in which the user is engaged;
      determine, in dependence on the activity in which the user is engaged and the portions of the user's body on which the user wearable devices are being worn, how to distribute sensing responsibilities for the multiple types of sensor data among the sensors of the plurality of user-wearable devices being worn by the user; and
      selectively activate and deactivating individual sensors of each of the user-wearable devices in dependence on results of the determination of how to distribute sensing responsibilities for the multiple types of sensor data among the sensors of the plurality of user-wearable devices being worn by the user;
      wherein when the base station determines that a same identified type of sensor data that is to be sensed is obtainable from a same type of sensor of more than one of the user-wearable devices, the base station is configured to determine a schedule that changes over time how the sensing responsibilities are distributed among the sensors of the plurality of user-wearable devices being worn by the user in order to increase how long each of the user-wearable devices can operate between battery charges or replacements, compared to if distribution of the responsibilities among the sensors of the plurality of user-wearable devices being worn by the user remained unchanged after an initial distribution was determined.

24. The system of claim 23, wherein the base station is also adapted to:
   receive the multiple types of sensor data from the user-wearable devices;
   track the one or more metrics, relevant to the activity in which the user is engaged, in dependence on sensor data received from the user-wearable devices; and
   provide user feedback in dependence on the tracked one or more metrics relevant to the activity in which the user is engaged, wherein the user feedback is indicative of the user's performance, indicative of the user's progress towards a goal, and/or includes advice for improving the user's performance.

25. The system of claim 23, wherein when the base station determines that a same identified type of sensor data that is to be sensed is obtainable from a same type of sensor of more than one of the user-wearable devices, the schedule that is determined by the base station ensures that no individual one of the sensors of the same type obtains the identified type of sensor data for more than a specified consecutive amount of time.

* * * * *

UNITED STATES PATENT AND TRADEMARK OFFICE
CERTIFICATE OF CORRECTION

PATENT NO. : 9,629,574 B2
APPLICATION NO. : 14/792386
DATED : April 25, 2017
INVENTOR(S) : Yong Jin Lee It is certified that error appears in the above-identified patent and that said Letters Patent is hereby corrected as shown below:

On the Title Page

Abstract (Line 4), please change "wirelessly" to -- wireless --.

In the Claims

Column 22, Line 15 (Claim 1, Line 14), please change "user wearable" to -- user-wearable --.
Column 22, Line 23 (Claim 1, Line 21), please change "user wearable" to -- user-wearable --.
Column 23, Line 36 (Claim 12, Line 1), please change "plurality" to -- plurality of --.
Column 23, Line 46 (Claim 12, Line 6), please change "to worn" to -- to be worn --.
Column 23, Line 60 (Claim 12, Line 25), please change "user wearable" to -- user-wearable --.
Column 23, Line 67 (Claim 12, Line 32), please change "user" to -- user- --.
Column 25, Line 24 (Claim 23, Line 3), please change "plurality" to -- plurality of --.
Column 25, Line 29 (Claim 23, Line 8), please change "to worn" to -- to be worn --.
Column 25, Line 40 (Claim 23, Line 19), please change "user wearable" to -- user-wearable --.
Column 25, Line 47 (Claim 23, Line 26), please change "user wearable" to -- user-wearable --.

Signed and Sealed this
Third Day of October, 2017

Joseph Matal
*Performing the Functions and Duties of the*
*Under Secretary of Commerce for Intellectual Property and*
*Director of the United States Patent and Trademark Office*